United States Patent [19]

Oda et al.

[11] Patent Number: 5,128,481
[45] Date of Patent: Jul. 7, 1992

[54] PYRAZOLYL DERIVATIVES

[75] Inventors: Masatsugu Oda; Toshiro Sakaki; Kazuhiko Kikutake, all of Yokohama, Japan

[73] Assignee: Mitsubishi Kasei Corporation, Tokyo, Japan

[21] Appl. No.: 734,292

[22] Filed: Jul. 17, 1991

Related U.S. Application Data

[62] Division of Ser. No. 625,762, Dec. 13, 1990, Pat. No. 5,055,477.

[30] Foreign Application Priority Data

Dec. 13, 1989 [JP] Japan .................. 1-323035
Mar. 28, 1990 [JP] Japan .................. 2-79763
Oct. 12, 1990 [JP] Japan .................. 2-273724
Nov. 27, 1990 [JP] Japan .................. 2-324113

[51] Int. Cl.$^5$ .................. C07D 231/18; C07D 417/12
[52] U.S. Cl. .................. 548/377; 546/279; 548/170; 548/186; 548/204; 548/374
[58] Field of Search .................. 546/279; 548/186, 377

[56] References Cited

FOREIGN PATENT DOCUMENTS 61358 5/1981 Japan .

Primary Examiner—Robert W. Ramsuer
Attorney, Agent, or Firm—Wenderoth, Lind & Ponack

[57] ABSTRACT

A pyrazolyl acrylic acid derivative having plant fungicidal activity of formula (I):

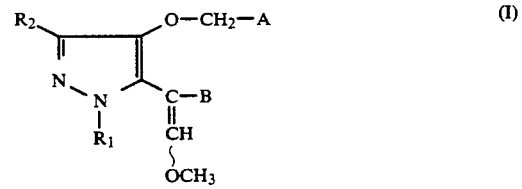

wherein:
$R_1$ and $R_2$ are independently hydrogen or $C_1$–$C_5$ alkyl;
A is a group of the formula:

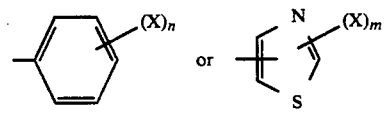

wherein X is independently hydrogen; halogen; cyano; nitro; $C_1$–$C_{10}$ alkyl, $C_2$–$C_{11}$ alkenyl, $C_1$–$C_{10}$ alkoxy, $C_2$–$C_{11}$ alkenyloxy, $C_2$–$C_{11}$ alkynyloxy, $C_2$–$C_{11}$ alkylcarbonyl or $C_2$–$C_{11}$ alkylcarbonyloxy optionally substituted with one or more substituents selected from halogen, nitro, cyano, trifluoromethyl and $C_1$–$C_5$ alkoxy; or $C_7$–$C_{13}$ arylcarbonyl, $C_4$–$C_9$ cycloalkylcarbonyloxy, $C_7$–$C_{13}$ arylcarbonyloxy, $C_6$–$C_{12}$ aryl, $C_6$–$C_{12}$ aryloxy, $C_2$–$C_{13}$ heteroaryl having 1–3 heteroatom(s) selected from oxygen, sulfur, and nitrogen, $C_2$–$C_{13}$ heteroaryloxy having 1–3 heteroatom(s) selected from oxygen, sulfur, and nitrogen, $C_7$–$C_{12}$ aralkyl or $C_7$–$C_{12}$ aralkyloxy optionally substitutes with one or more substituents selected from halogen, nitro, cyano, trifluoromethyl, $C_1$–$C_5$ alkyl, and $C_1$–$C_5$ alkoxy; m is 1 or 2; and n is an integer of 1–5; or two Xs may form a fused ring together with the benzene ring or thiazole ring to which they are attached; and
B is methoxycarbonyl or cyano.

2 Claims, No Drawings

PYRAZOLYL DERIVATIVES

This application is a division of application Ser. No. 07/625,762, filed Dec. 13, 1990 now U.S. Pat. No. 5,055,477.

This invention provides new pyrazolyl acrylic acid derivatives, processes for producing said compounds, and intermediates useful in those processes. The present invention also provides agricultural/horticultural fungicides which contain the derivatives, as an active ingredient and are capable of controlling various phytopathogens.

It has been recognized that a class of acrylic acid derivatives have biological activities including fungicidal activities. Among them, a compound of the formula:

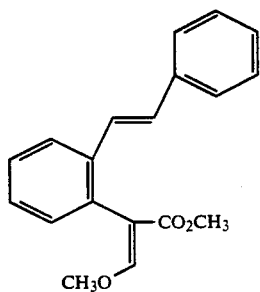

is described in European Patent Publication No. 178826, and compounds of the formula:

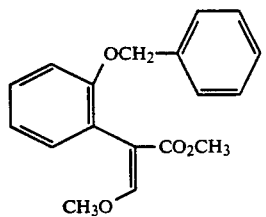

and

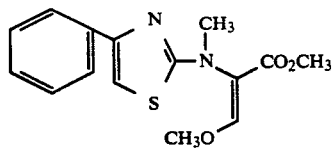

are described in Japanese Patent Publications (kokai) Nos. 277652/1986 and 254669/1989, respectively. As will be hereinafter discussed, these existing compounds are not sufficient effective enough in terms of fungicidal and systemic activity as agricultural/horticultural fungicides.

It has now been found that a class of pyrazolyl acrylic acid derivatives have a potent fungicidal activity as well as strong systemic activity.

Thus, the present invention provides novel agriculturally- and horticulturally-useful pyrazolyl acrylic acid derivatives of formula (I):

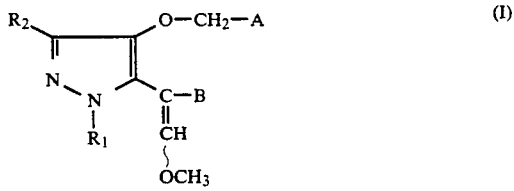

wherein:
$R_1$ and $R_2$ are independently hydrogen or $C_1$–$C_5$ alkyl;
A is a group of formula:

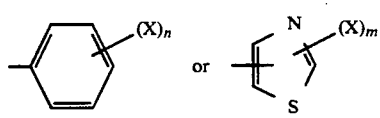

wherein X is independently hydrogen; halogen; cyano; nitro; $C_1$–$C_{10}$ alkyl, $C_2$–$C_{11}$ alkenyl, $C_1$–$C_{10}$ alkoxy, $C_2$–$C_{11}$ alkenyloxy, $C_2$–$C_{11}$ alkynyloxy, $C_2$–$C_{11}$ alkylcarbonyl or $C_2$–$C_{11}$ alkylcarbonyloxy optionally substituted with one or more substituents selected from halogen, nitro, cyano, trifluoromethyl and $C_1$–$C_5$ alkoxy; or $C_7$–$C_{13}$ arylcarbonyl, $C_4$–$C_9$ cycloalkylcarbonyloxy, $C_7$–$C_3$ arylcarbonyloxy, $C_6$–$C_{12}$ aryl, $C_6$–$C_{12}$ aryloxy, $C_2$–$C_{13}$ heteroaryl having 1–3 heteroatom(s) selected from oxygen, sulfur, and nitrogen, total number of atoms of said heteroaryl being 5–14, $C_2$–$C_{13}$ heteroaryloxy having 1–3 heteroatom(s) selected from oxygen, sulfur, and nitrogen, total number of atoms of said heteroaryloxy being 5–14, $C_7$–$C_{12}$ aralkyl or $C_7$–$C_{12}$ aralkyloxy optionally substituted with one or more substituents selected from halogen, nitro, cyano, trifluoromethyl, $C_1$–$C_5$ alkyl, and $C_1$–$C_5$ alkoxy; m is 1 or 2; and n is an integer of 1–5; or two Xs may form a fused ring together with the benzene ring or thiazole ring to which they are attached; and B is methoxycarbonyl or cyano.

The present invention also provides fungicidal compositions comprising a compound of formula (I) and agriculturally-acceptable inert carrier therefor.

For the purpose of the present invention, as disclosed and claimed herein, the following terms are defined as below.

In the definition of $R_1$ and $R_2$, the term "$C_1$–$C_5$ alkyl" includes, for example, methyl, ethyl, n-propyl, isopropyl, n-butyl, t-butyl, n-pentyl, isopentyl, t-pentyl, neopentyl, 1-methylbutyl, and the like. $R_1$ is preferably hydrogen or $C_1$–$C_4$ alkyl, more preferably methyl or ethyl, and $R_2$ is preferably hydrogen or $C_1$–$C_3$ alkyl, more preferably methyl, ethyl or propyl.

In the definition of X, the term "$C_1$–$C_{10}$ alkyl" includes, for example, methyl, ethyl, n-propyl, isopropyl, n-butyl, t-butyl, n-pentyl, isopentyl, t-pentyl, neopentyl, 1-methylbutyl, 1,2-dimethylbutyl, hexyl, heptyl, octyl, nonyl, decyl, and the like; the term "$C_2$–$C_{11}$ alkenyl" includes, for example, vinyl, allyl, 1-propenyl, 2-butenyl, 1,3-butadienyl, 2-pentenyl, and the like; the term "$C_1$–$C_{10}$ alkoxy" includes methoxy, ethoxy, propoxy, isopropoxy, n-butoxy, and the like; the term "$C_2$–$C_{11}$ alkynyloxy" includes, for example, propargyloxy, and the like; the term "$C_2$–$C_{11}$ alkylcarbonyl" includes, for example, acetyl, propionyl, butyryl, and the like; the term "$C_7$-$C_{13}$ arylcarbonyl" includes, for example, benzoyl, toluoyl, naphthoyl, and the like; the term "$C_2$-$C_{11}$ alkylcarbonyloxy" includes, for example, acetoxy, propionyloxy, butyryloxy, and the like; the term "$C_4$-$C_9$ cycloalkylcarbonyloxy" includes, for example, cyclohexanecarbonyloxy, and the like; the term "$C_7$-$C_{13}$ arylcarbonyloxy" includes, for example, benzoyloxy, torylcarbonyloxy, and the like; the term "$C_6$-$C_{12}$ aryl" includes, for example, phenyl, toryl, xylyl, naphthyl, and the like; the term "$C_6$-$C_{12}$ aryloxy" includes, for example, phenoxy, toryloxy, naphthyloxy, and the like; the term "$C_2$-$C_{13}$ heteroaryl" includes, for example, thiazolyl, benzothiazolyl, pyridyl, pyrazolyl, and the like; the term "$C_2$-$C_{13}$ heteroaryloxy" includes, for example, thiazolyloxy, benzothiazolyloxy, pyridyloxy, and the like; the term "$C_7$-$C_{12}$ aralkyl" includes, for example, benzyl, phenethyl, and the like; the term "$C_7$-$C_{12}$ aralkyloxy" includes, for example, benzyloxy, phenethyloxy, and the like; the term "halogen" includes fluorine, chlorine, bromine and iodine.

X is preferably hydrogen; halogen; cyano; nitro; optionally substituted $C_1$-$C_4$ alkyl, $C_2$-$C_3$ alkenyl, $C_1$-$C_3$ alkoxy, $C_2$-$C_3$ alkenyloxy, $C_2$-$C_3$ alkynyloxy, or $C_2$-$C_5$ alkylcarbonyloxy optionally substituted with one or more substituents selected from halogen, nitro, cyano, and trifluoromethyl; or phenyl, phenoxy, benzyl, benzyloxy, thiazolyl, thiazolyloxy, pyridyloxy, benzoyl, or benzothiazolyloxy optionally substituted with one or more substituents selected from halogen, nitro, cyano, trifluoromethyl, $C_1$-$C_4$ alkyl, and $C_1$-$C_5$ alkoxy. More preferably, X is hydrogen, fluorine, chlorine, bromine, cyano, nitro, optionally substituted methyl, butyl, optionally substituted methoxy, optionally substituted ethoxy, optionally substituted propoxy, optionally substituted propenyloxy, propargyloxy, butylyloxy, optionally substituted phenyl, optionally substituted phenoxy, optionally substituted benzyl, benzyloxy, thiazolyloxy, benzothiazolyloxy, optionally substituted pyridyloxy, or benzoyl. Preferred substituents for methyl, methoxy, ethoxy, propoxy and propenyloxy groups include fluorine and chlorine. Preferred substituents for phenyl, phenoxy, benzyl, and pyridyloxy include methyl, butyl, methoxy, fluorine, chlorine, nitro and trifluoromethyl.

When adjacent X forms a fused ring together with the benzene ring or thiazol ring to which they are attached, the fused ring may be preferably 2,3-dihydrobenzofuran, chroman, naphthalene, fluorene, anthraquinone, or benzo-1,3-dioxole.

Therefore, preferred compounds (I) are those of formula (I), as defined above, in which A is a group of formula:

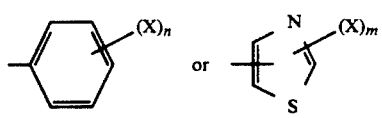

wherein X is independently hydrogen; halogen; cyano; nitro; $C_1$-$C_4$ alkyl, $C_2$-$C_3$ alkenyl, $C_1$-$C_3$ alkoxy, $C_2$-$C_3$ alkenyloxy, $C_2$-$C_3$ alkynyloxy, or $C_2$-$C_5$ alkylcarbonyloxy optionally substituted with one or more substituents selected from halogen, nitro, cyano, and trifluoromethyl; or phenyl, phenoxy, benzyl, benzyloxy, thiazolyl, thiazolyloxy, pyridyloxy, benzoyl, or benzothiazolyloxy optionally substituted with one or more substituents selected from halogen, nitro, cyano, trifluoromethyl, $C_1$-$C_4$ alkyl and $C_1$-$C_4$ alkoxy; m is 1 or 2; and n is a integer of 1-5; or two Xs may form a fused ring together with the benzene ring or thiazole ring to which they are attached, where the fused ring is selected from 2,3-dihydrobenzofuran, chroman, naphtalene, fluorene, anthraquinone or benzo-1,3-dioxole.

All the compounds of the invention are novel and can be prepared according to the general process described below:

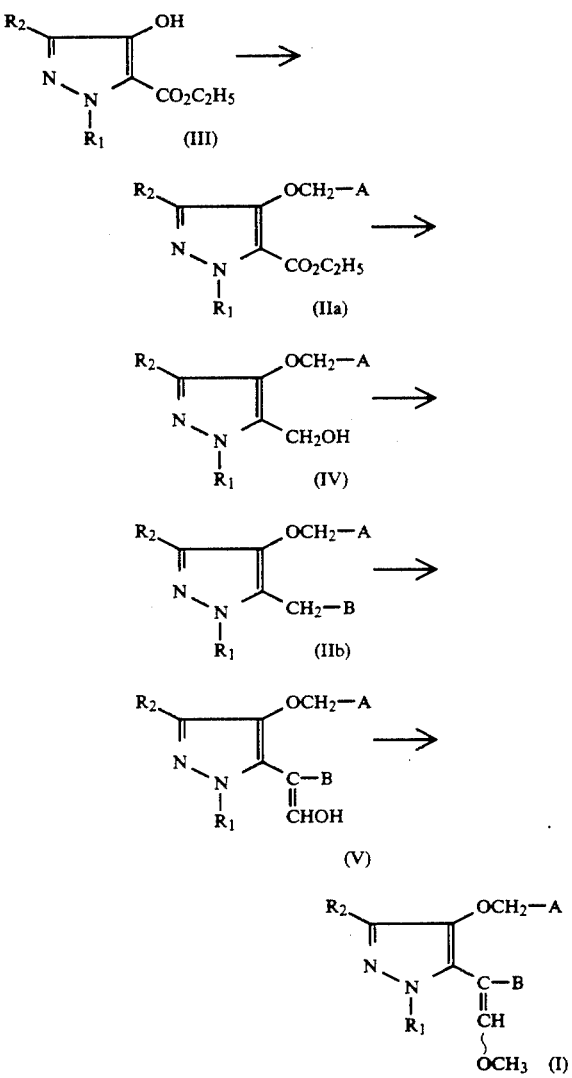

wherein, $R_1$, $R_2$, A and B are as defined above.

The required starting material of formula (III) can be readily synthesized using any of known methods described in literatures such as Tetrahedron Letters, No. 19, 1591-2 (1971).

The ester of formula (IIa), one of the key compound as an intermediate in the process of the invention, can be prepared by reacting the compound (III) in the presence of a base in an inert solvent with the compound of formula:

A—CH$_2$—hal wherein, A is as defined above, and hal is a leaving group such as halogen atom, toluenesulphonyloxy or methanesulphonyloxy group. Inert solvents which may be used include dimethylformamide, dimethylsulfoxide, toluene, tetrahydrofuran and diisopropyl ether. Bases which can be used include sodium hydride, potassium carbonate and sodium ethylate.

The alcohol (IV) can be obtained by reducing ester (IIa) with a reducing agent such as lithium aluminium hydride, metal sodium or sodium borohydride, or with various hydrogenation catalysts. The alcohol (IV) is then halogenated with a haloganating agent such as hydrochloride, thionylchloride, phosphorus oxychloride or phosphorus tribromide, which is followed by substitution with cyanide such as sodium cyanide, potassium cyanide or trimethylsilylnitrile to give the nitrile (IIb), the intermediate of the invention.

The reduction for obtaining the ester (IIa) from the alcohol (IV) can be carried out using any of known procedures described in literatures such as *Organic Synthesis*, Col. Vol. II, p. 468; ibid, Col. Vol. II, p. 325; ibid, Col. Vol. IV, p. 834, or those analogous to them.

The halogenation can be carried out using any of known methods described in literatures such as *Organic Synthesis*, Col. Vol. IV, p. 576; ibid, Col. Vol. VI, p. 169; *Tetrahedron Letters*, No. 10, p. 901–904 (1978), or those analogous to them.

The cyanogenation for obtaining the nitrile (IIb) from the alcohol (IV) can be carried out using any of known methods described in literatures such as *Organic Synthesis*, Col. Vol. I, p. 107; *Kagaku no Ryouiki Zokan*, No. 125, p. 155-175 (1980); or those analogous to them.

The nitrile (IIb) is converted, if desired, into methyl ester by reacting it with methanol and/or water in the presence of hydrochloric acid or sulfuric acid. The esterification can be carried out using any of known methods described in literatures such as *J. Chem. Soc.*, 2417 (1963); *J. Org. Chem.*, 23 (1958); *Ber.*, 105, 1778 (1972); and *Organic Synthesis*, Col. Vol. I, p. 270, or those analogous to them.

According to the process of the invention, the intermediate (IIb) is then reacted with methyl formate and a base in the presence or absence of an inert solvent to give a compound of formula (V) or its salt. The compound (V) or its salt, when reacted with a methylation reagent under basic conditions in the presence or absence of an inert solvent, gives the compound of the invention of formula (I).

The above-mentioned reaction can be carried out at a temperature in the range of about −78° C. to the boiling point of the solvent to be used, preferably 0° to 150° C.

Inert solvents which may be used include aromatic hydrocarbons such as benzene, toluene, and the like; ethers such as diethyl ether, tetrahydrofuran, and the like; polar solvents such as dimethylformamide, dimethyl sulfoxide, water, and the like; alcohols such as methanol, and the like; or a mixture comprising two or more of them.

Bases which may be used include tertiary amines such as N-methylmorpholine, triethylamine, and the like; aromatic bases such as pyridine, picoline, N,N-diethylaniline, and the like; alkaline metal hydroxides such as sodium hydroxide, and the like; alkaline metal hydrides such as sodium hydride, and the like; alkaline metal alcohlates such as sodium methylate, and the like; alkaline metal carbonates or alkaline metal hydrogen carbonate such as potassium carbonate or sodium hydrogen carbonate, and the like.

Methylation reagents include methyl iodide, dimethyl sulfate, and the like.

Alternatively, the compound (I) of the invention can be prepared according to the following reaction scheme.

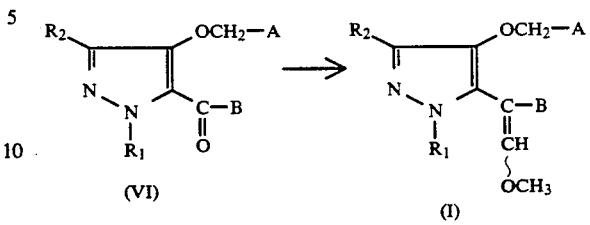

wherein, $R^1$, $R^2$, A and B are as defined above.

The required α-keto-ester derivative of formula (VI) can be readily synthesized using known procedures described, for instance, in *Synth. Commun.*, 11, 943 (1981), or those analogous to them. The compound (VI) can be prepared by the reaction between a corresponding pyrazolyl-magnesium halide derivative or pyrazolyl-lithium derivative with dimethyl oxalate. Alternatively, the compound (VI) can be prepared by oxidizing an acetate derivative of the compound of formula (IIb) with an appropriate oxidizing agent such as selenium dioxide, and the like.

The compound of formula (VI) can be converted into the compound of formula (I) through the Wittig Reaction using a corresponding Wittig reagent in an appropriate solvent. the Wittig reagents are available by any of known methods, for example, by reacting a base to triphenylphosphonium halide which can be prepared from methoxymethyl chloride by any of known procedures.

Each reaction can be carried out at a temperature in the range of about −78° C. to the boiling point of the solvent to be used, preferably −20° to 150° C.

Bases which may be used include alkali metal-containing bases such as sodium hydride, metal sodium, sodium amide, sodium dimethylsulfonate, and the like; alkaline metal alcoholates such as sodium methylate, and the like; alkyl lithium such as lithium butylate, and the like; tertiary amines such as triethylamine, and the like.

Solvents which may be used include ethers such as diethyl ether, tetrahydrofuran, and the like; polar solvents such as dimethylformamide, dimethyl sulfoxide, and the like.

Thus, the present invention provides a process for preparing a compound of formula (I), as defined above, which process comprises the steps;

(a) reacting a compound of the formula (IIb);

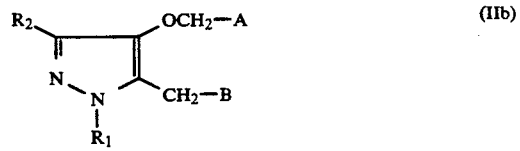

wherein $R_1$, $R_2$, A and B are as previously defined, with methyl formate and a base; and (b) reacting the compound obtained in step (a) or its salt with a methylation reagent in the presence or absence of a base.

The present invention further provides another process for preparing the compound of formula (I), which comprises reacting a compound of the formula (VI):

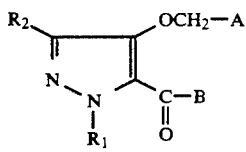

(VI)

wherein $R_1$, $R_2$, A and B are as previously defined, with a Wittig reagent in an appropriate solvent.

The pyrazole derivatives (IIb) and (VI) are novel and useful intermediates in the process for preparing the compounds (I) of the invention. Thus, the present invention also provides the pyrazole derivatives of formula (II):

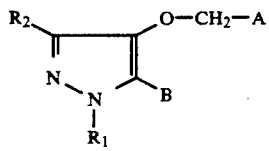

(II)

wherein $R_1$, $R_2$ and A are as defined above, and E is ethoxycarbonyl or —$CH_2$—B where B is as defined above.

All the compounds of formula (I) are novel and have been demonstrated to be agriculturally- and horticulturally-useful. The compounds of the invention possess outstanding characteristics essential for fungicides, that is, high activity in controlling phytopathogens and strong systemic activity. Main pathogens to be controlled are *Pyricularia oryzae* (rice blast), *Rhizoctonia solani* (sheath blight of rice), *Puccinia recondita* (leaf rusts of wheat), *Botrytis cinerea* (gray mold of vegetables or fruit-trees) and *Phytophthora infestance* (late blight of tomato and potato).

Furthermore, the compounds (I) are low in toxicity to human being and linestock and fishes as well, so that they are extremely useful as an active ingredient for the plant fungicides.

The active compound (I) can be used alone without any further treatments for the purpose of controlling diseases. However, it is preferably formulated into a composition of an appropriate form by known procedures using agriculturally-acceptable inert adjuvants so that the active ingredient can disperse effectively upon application. Examples of adjuvants to be used in the present compositions are solvents, carriers, fillers and surfactants. Appropriate forms of the fungicidal compositions are, for example, emulsifiable concentrates, wettable powders and dusts.

Examples off suitable solvents include water; alcohols such as methanol, ethanol, ethylene glycol, and the like; ketons such as aceton, methyl ethyl keton, cyclohexanone, and the like; ethers such as diethyl ether, dioxane, cellosolve, and the like; aliphatic hydrocarbons such as kerosene, fuel oil, and the like; aromatic hydrocarbons such as benzene, toluene, xylene, solvent naphtha, methyl naphthalene, and the like; hydrocarbon halides such as dichloroethane, trichlorobenzene, carbon tetrachloride, and the like; acid amides such as dimethylformamide, and the like; esters such as ethyl acetate, butyl acetate, glycerol esters of fatty acids, and the like; nitriles such as acetonitrile, and the like. The solvents may be used alone or as a mixture comprising two or more of them.

Examples of suitable fillers include clays such as kaolin, bentonite, and the like; talcs such as talc, pyrophyllite, and the like; mineral powders such as diatomaceous, oxides including white carbon, and the like; and powders derived from plants such as soybean powder, carboxymethyl cellulose (CMC), and the like. These fillers may be used alone or as a mixture comprising two or more of them.

Surfactants serve as spreading agents, dispersing agents emulsifying agents or penetrating agents. Examples of surfactants include nonionic surfactants such as polyoxyethylene alkylallyl ether, polyoxyethylene sorbitan monolaurate, and the like; cationic surfactants such as alkyldimethylbenzylammonium chloride, alkylpyridinium chloride, and the like; anionic surfactants such as alkylbenzene sulfonate, lignosulfonate, higher alcohol sulfate; amphoteric surfactants such as alkyldimethyl betain, dodesylaminoethyl glycine, and the like. These surfactants can be used alone or as a mixture comprising two or more of them.

When the compounds of the invention are used in the form of emulsion, the fungicidal compositions of the invention are usually concentrated formulations which are diluted with water before use to obtain an emulsion containing the active compound at a suitable concentration for application, for example, spray application. The concentrated emulsifiable formulations generally contain about 5 to about 80 parts, preferably about 10 to about 70 parts, of the active compounds of the invention, about 10 to about 90, preferably about 20 to about 80 parts, of solvent and about 3 to about 20, preferably about 5 to about 15 parts, of surfactants.

When the compounds of the invention are used in the form of wettable powders, the composition of the invention can be formulated in a mixture which contain about 5 to about 80 parts, preferably about 10 to about 70 parts, of the active compound, about 10 to about 90 parts, preferably about 20 to about 80 parts, of fillers and about 1 to about 20 parts, preferably about 3 to about 15 parts, of surfactants. The wettable powders are also diluted with a solvent such as water before use to obtain a suitable solution.

When the compounds of the invention are used in the form of dusts, the formulations of the invention are prepared simply by intimately mixing about 0.1 to about 10 parts, preferably about 1 to about 5 parts, of the active compound with about 90 to about 99.9 parts, preferably about 95 to about 99 parts, of suitable fillers such as kaolin, bentonite, talc, and the like.

The compositions of the invention may additionally contain other active substances such as another fungicides, insecticides, acaricides, and the like, provided that they are no longer inhibitory to the fungicidal action of the compounds (I).

As for the way of application of the fungicide of this invention, it can be effectively applied either by spraying or dusting to plants or by application to water surface. In case of stem-foliar spray, emulsifiable concentrated formulation or wettable powder of the invention is diluted with water so as to give a emulsion or solution containing about 10 to about 1000 ppm of active compounds. In general, the application rate of so prepared emulsions or solutions ranges from about 0.5 to about 50 L/are (i.e., about 1 to about 20 L/acre).

The following examples further illustrate the compound of the invention and the process preparing the same. The examples are not intended to be limiting to the scope of the invention in any respect and should not so construed. All the compounds prepared in the examples were confirmed on the basis of elemental analysis, and IR and NMR spectroscopies.

EXAMPLE 1

Preparation of (E)-methyl 2-(4-benzyloxy-1,3-dimethylpyrazol-5-yl)-3-methoxyacrylate (compound No. 1 in the Table 1)

To a 5 ml solution of ethyl 1,3-dimethyl-4-hydroxypyrazole-5-carboxylate (2 g, 11.6 mmol) in anhydrous dimethylformamide (hereinafter, referred to as DMF) was added sodium hydride (60% dispersion in oil) (0.47 g, 11.8 mmol) under ice-cooling. Benzyl bromide (2 g, 11.7 mmol) was then added dropwise thereto, and the resulting mixture was stirred at room temperature for one hour and poured into water. The mixture was extracted with ethyl acetate. The extract was washed with water, and saturated brine, dried over anhydrous sodium sulfate and concentrated in vacuo. The residue was chromatographed over silica gel (eluent; ethyl acetate/n-hexane=1:4) to give ethyl 4-benzyloxy-1,3-dimethylpyrazol-5-carboxylate (2.5 g, 9.1 mmol, 78%).

NMR (90 MHz, CDCl₃) δ ppm: 1.35 (3H, t), 2.05 (3H, s), 4.05 (3H, s), 4.40 (2H, q), 5.0 (3H, s), 7.45 (5H).

To a 15 ml solution of ethyl 4-benzyloxy-1,3-dimethylpyrazol-5-carboxylate (2.5 g, 9.1 mmol) in anhydrous tetrahydrofuran (hereinafter, referred to as THF) was added lithium aluminium hydride (0.2 g, 5.3 mmol) under ice-cooling. After stirring at room temperature for one hour, the reaction mixture was poured into water. The mixture was extracted with ethyl acetate, and the extract was successively washed with water and saturated brine, dried over anhydrous sodium sulfate and concentrated in vacuo. To the residue (2 g) was added toluene (5 ml) and thionyl chloride (2 g) and the resulting mixture was heated under reflux for one hour. After low boiling substances were evaporated, the residue was combined with ethyl acetate. The mixture was successively washed with, water, aqueous sodium bicarbonate, water, and saturated brine, dried over anhydrous sodium sulfate and concentrated in vacuo. To a 5 ml solution of the residue in dimethyl sulfoxide (hereinafter, referred to as DMSO) was added sodium cyanide (0.43 g, 8.8 mmol) and the mixture was stirred at room temperature and left to stand overnight. The reaction mixture was poured into water. The mixture was extracted with ethyl acetate, and the extract was successively washed with water, and saturated brine, dried over anhydrous sodium sulfate and concentrated in vacuo. The residue was chromatographed over silica gel (eluent; ethyl acetate/n-hexane=1:2) to obtain (4-benzyloxy-1,3-dimethylpyrazol-5-yl)acetonitrile (1.6 g, 6.6 mmol, 73%).

NMR (90 MHz, CDCl₃) δ ppm: 2.2 (3H, s), 3.35 (3H, s), 3.8 (3H, s), 4.9 (2H, s), 7.42 (5H).

Concentrated sulfuric acid was added to a solution of methanol (9.5 ml) and water (0.5 ml) under ice-cooling, and (4-benzyloxy-1,3-dimethylpyrazol-5-yl)acetonitrile (1.6 g, 6.6 mmol) was added thereto and the resulting mixture was heated for 6 hours under reflux. It was then concentrated in vacuo to remove methanol. The residue was diluted with ethyl acetate, successively washed with water, aqueous sodium bicarbonate, water, and saturated brine, dried over anhydrous sodium sulfate and concentrated in vacuo. The residue was chromatographed over silica gel (eluent; ethyl acetate/n-hexane=1:2) to obtain methyl (4-benzyloxy-1,3-dimethylpyrazol-5-yl)acetate (0.6 g, 2.2 mmol, 33%).

NMR (90 MHz, CDCl₃) δ ppm: 2.15 (3H, s), 3.5 (3H, s), 3.7 (3H, s), 4.88 (2H, s), 7.42 (5H).

A solution of methyl (4-benzyloxy-1,3-dimethylpyrazol-5-yl)acetate (2.5 g, 9.1 mmol) and methyl formate (15 g, 250 mmol) in anhydrous DMF (10 ml) was added dropwise to a suspension of sodium hydride (60% dispersion in oil) (0.55 g, 13.8 mmol) in anhydrous DMF (5 ml), while the temperature being maintained below 10° C. by cooling on ice. After stirring at room temperature for 2 hours, the low boiling substances were removed under reduced pressure. To the residue was added potassium carbonate (2.5 g, 18.1 mmol), dimethyl sulfate (2.3 g, 18.2 mmol), and DMF (5 ml) under ice-cooling. After stirring at room temperature for 3 hours, the mixture was distilled under reduced pressure to remove low boiling substances. The residue was diluted with ethyl acetate, successively washed with water, and saturated brine, dried over anhydrous sodium sulfate and concentrated under reduced pressure. The residue was chromatographed over silica gel (eluent; ethyl acetate/n-hexane=1:1) to obtain (E)-methyl 2-(4-benzyloxy-1,3-dimethylpyrazol-5-yl)-3-methoxyacrylate (compound No. 1 in the Table 1) as a clear oil (2.1 g, 73%). Corresponding compound in Z-form (compound No. 2 in the Table 1) was also produced by the above reaction and recovered from the column.

According to the procedures described in the above Example 1, compounds No. 3–8 and 12–115 listed in the following Table 1 were prepared.

EXAMPLE 2

Preparation of (E)-methyl 2-{1,3-dimethyl-4-[1-(2-methylthiazol-4-yl)-methyloxy]pyrazol-5-yl}-3-methoxyacrylate (compound No. 9 in Table 1)

To a suspension of methoxymethyltriphenylphosphonium chloride (2 g, 5.84 mmol) in anhyrous THF was added 3.5 ml solution of lithium n-butylate (1.6 mol) in hexane. After stirring at room temperature for 30 minutes, methyl {1,3-dimethyl-4-[1-(2-methylthiazol-4-yl)methyloxy]pyrazol-5-yl}glyoxalate (0.6 g, 1.95 mmol) in anhydrous THF (6 ml) was added thereto and the mixture was allowed to stand for two hours. The reaction mixture was poured into water and extracted with ethyl acetate. The extract was washed with water and saturated brine, dried over magnesium sulfate and concentrated in vacuo. The residue was chromatographed over silica gel to obtain (E)-methyl 2-{1,3-dimethyl-4-[1-(2-methylthiazol-4-yl)methyloxy]-pyrazol-5-yl}-3-methoxyacrylate (compound No. 9 in Table 1) as an oil (0.25 g, 38.1%).

According to the procedures described in the above Example 2, compounds No. 10 and 11 in Table 1 were prepared.

The following Table 1 shows the compounds (I) of the invention obtained in the same manner as described in the above Examples 1 and 2. Table 2 shows examples of compounds (I) which are further obtainable according to the procedures described in Examples 1 and 2. Typical intermediates (II) used in the preparation of compounds (I) listed in the Table 1 are shown in the Table 4 with their physicochemical properties.

TABLE 1

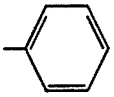

| Compound No. | R₁ | R₂ | A | B | isomer* | Physico-chemical properties |
|---|---|---|---|---|---|---|
| 1 | —CH$_3$ | —CH$_3$ | 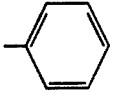 | —CO$_2$CH$_3$ | E | oil |
| 2 | —CH$_3$ | —CH$_3$ | 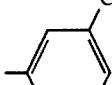 | —CO$_2$CH$_3$ | Z | oil |
| 3 | —CH$_3$ | —CH$_3$ | 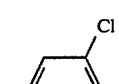 (Cl) | —CO$_2$CH$_3$ | E | oil |
| 4 | —CH$_3$ | —CH$_3$ | 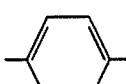 (Cl) | —CO$_2$CH$_3$ | Z | m.p. 90~92.5° C. |
| 5 | —CH$_3$ | —CH$_3$ | 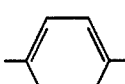 (t-Bu) | —CO$_2$CH$_3$ | E | oil |
| 6 | —CH$_3$ | —CH$_3$ | 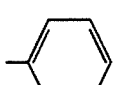 (t-Bu) | —CO$_2$CH$_3$ | Z | oil |
| 7 | —CH$_3$ | —CH$_3$ | 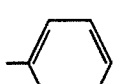 | —CN | E | oil |
| 8 | —CH$_3$ | —CH$_3$ | 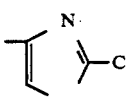 | —CN | Z | m.p. 63~66° C. |
| 9 | —CH$_3$ | —CH$_3$ | 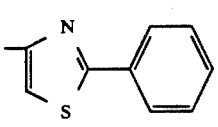 (thiazole-CH$_3$) | —CO$_2$CH$_3$ | E | oil |
| 10 | —CH$_3$ | —CH$_3$ | 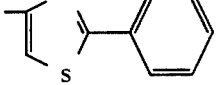 (thiazole-Ph) | —CO$_2$CH$_3$ | E | oil |
| 11 | —CH$_3$ | —CH$_3$ | (thiazole-Ph) | —CO$_2$CH$_3$ | Z | viscous liquid |

TABLE 1-continued
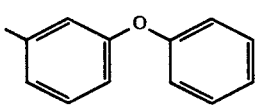
| Compound No. | R₁ | R₂ | A | B | isomer* | Physico-chemical properties |
|---|---|---|---|---|---|---|
| 12 | —CH₃ | —CH₃ | 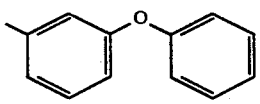 | —CO₂CH₃ | E | oil |
| 13 | —CH₃ | —CH₃ | 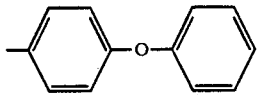 | —CO₂CH₃ | Z | oil |
| 14 | —CH₃ | —CH₃ | 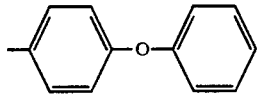 | —CO₂CH₃ | E | oil |
| 15 | —CH₃ | —CH₃ | 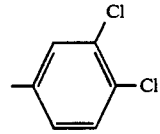 | —CO₂CH₃ | Z | viscous liquid |
| 16 | —CH₃ | —CH₃ |  | —CO₂CH₃ | E | oil |
| 17 | —CH₃ | —C₂H₅ |  | —CO₂CH₃ | E | oil |
| 18 | —CH₃ | —C₂H₅ | 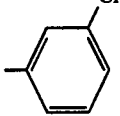 | —CO₂CH₃ | Z | oil |
| 19 | —CH₃ | —C₂H₅ | 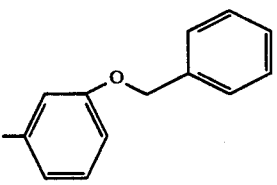 | —CO₂CH₃ | E | oil |
| 20 | —CH₃ | —C₂H₅ |  | —CO₂CH₃ | E | oil |
| 21 | —CH₃ | i-C₃H₇ |  | —CO₂CH₃ | E | oil |

TABLE 1-continued
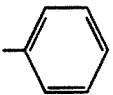
| Compound No. | $R_1$ | $R_2$ | A | B | isomer* | Physico-chemical properties |
|---|---|---|---|---|---|---|
| 22 | —CH$_3$ | i-C$_3$H$_7$ | 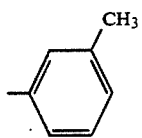 | —CO$_2$CH$_3$ | Z | oil |
| 23 | —CH$_3$ | —CH$_3$ | 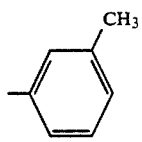 (3-CH$_3$) | —CO$_2$CH$_3$ | E | oil |
| 24 | —CH$_3$ | —CH$_3$ | 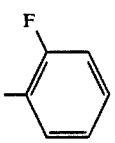 (3-CH$_3$) | —CO$_2$CH$_3$ | Z | oil |
| 25 | —CH$_3$ | —CH$_3$ | 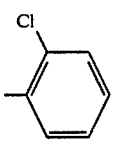 (2-F) | —CO$_2$CH$_3$ | E | oil |
| 26 | —CH$_3$ | —CH$_3$ | 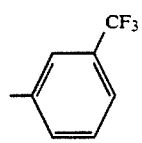 (2-Cl) | —CO$_2$CH$_3$ | E | oil |
| 27 | —CH$_3$ | —CH$_3$ | 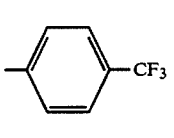 (3-CF$_3$) | —CO$_2$CH$_3$ | E | oil |
| 28 | —CH$_3$ | —CH$_3$ | 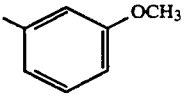 (4-CF$_3$) | —CO$_2$CH$_3$ | E | oil |
| 29 | —CH$_3$ | —CH$_3$ | 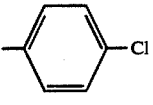 (3-OCH$_3$) | —CO$_2$CH$_3$ | E | oil |
| 30 | —CH$_3$ | —CH$_3$ | 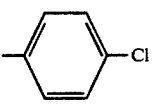 (4-Cl) | —CO$_2$CH$_3$ | E | oil |
| 31 | —CH$_3$ | —CH$_3$ | (4-Cl) | —CO$_2$CH$_3$ | Z | m.p. 98–100° C. |

TABLE 1-continued

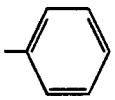

| Compound No. | R₁ | R₂ | A | B | isomer* | Physico-chemical properties |
|---|---|---|---|---|---|---|
| 32 | —$C_2H_5$ | —$CH_3$ | phenyl | —$CO_2CH_3$ | E | oil |
| 33 | —$C_2H_5$ | —$CH_3$ | phenyl | —$CO_2CH_3$ | Z | oil |
| 34 | —$C_2H_5$ | —$CH_3$ | 3-chlorophenyl | —$CO_2CH_3$ | E | oil |
| 35 | —$C_2H_5$ | —$CH_3$ | 3-phenoxyphenyl | —$CO_2CH_3$ | E | oil |
| 36 | —$CH_3$ | —$CH_3$ | 2,4-dimethylphenyl | —$CO_2CH_3$ | E | oil |
| 37 | —$CH_3$ | —$CH_3$ | 4-(4-trifluoromethylphenoxy)phenyl | —$CO_2CH_3$ | E | $n_D^{25}$ 1.5445 |
| 38 | —$CH_3$ | —$CH_3$ | 3-(6-trifluoromethylpyridin-2-yloxy)phenyl | —$CO_2CH_3$ | E | viscous liquid |
| 39 | —$CH_3$ | —$CH_3$ | 3-cyanophenyl | —$CO_2CH_3$ | E | oil |
| 40 | —$CH_3$ | —$CH_3$ | 3-(3-trifluoromethylphenoxy)phenyl | —$CO_2CH_3$ | E | viscous liquid |

TABLE 1-continued

Structure:
$R_2$ and $OCH_2-A$ on pyrazole ring; N-N with $R_1$; C=B; =CH-$OCH_3$

| Compound No. | $R_1$ | $R_2$ | A | B | isomer* | Physico-chemical properties |
|---|---|---|---|---|---|---|
| 41 | —CH₃ | —CH₃ | 2-fluoro-5-methylphenyl phenyl ether | —CO₂CH₃ | E | $n_D^{25}$ 1.5762 |
| 42 | —CH₃ | —CH₃ | 2,4-dimethylphenyl | —CO₂CH₃ | E | $n_D^{25}$ 1.5490 |
| 43 | —CH₃ | —CH₃ | 3-methylphenyl 4-nitrophenyl ether | —CO₂CH₃ | E | viscous liquid |
| 44 | —CH₃ | —CH₃ | 3-methylphenyl O-CH₂-CH=CCl₂ | —CO₂CH₃ | E | $n_D^{25}$ 1.5524 |
| 45 | —CH₃ | —CH₃ | 3-methylphenyl 3-chloro-5-trifluoromethyl-2-pyridyl ether | —CO₂CH₃ | E | viscous liquid |
| 46 | —CH₃ | —CH₃ | 2,4-dichlorophenyl | —CO₂CH₃ | E | oil |
| 47 | —CH₃ | —CH₃ | 3-methylphenyl 4-methoxyphenyl ether | —CO₂CH₃ | E | oil |

TABLE 1-continued

Structure:
$R_2$ at pyrazole 3-position, $OCH_2-A$ at 4-position, $C-B$ at 5-position with =CH-OCH$_3$, N-N with $R_1$ on N1.

| Compound No. | $R_1$ | $R_2$ | A | B | isomer* | Physico-chemical properties |
|---|---|---|---|---|---|---|
| 48 | —CH$_3$ | —CH$_3$ | 3-(4-chlorophenoxy)phenyl | —CO$_2$CH$_3$ | E | viscous liquid |
| 49 | —CH$_3$ | —CH$_3$ | 3-(3,4-dichlorophenoxy)phenyl | —CO$_2$CH$_3$ | E | viscous liquid |
| 50 | —CH$_3$ | —CH$_3$ | 3-(4-trifluoromethylphenoxy)phenyl | —CO$_2$CH$_3$ | E | viscous liquid |
| 51 | —CH$_3$ | —CH$_3$ | 3-(2-nitrophenoxy)phenyl | —CO$_2$CH$_3$ | E | viscous liquid |
| 52 | —CH$_3$ | —CH$_3$ | 3-(2-chloro-4-trifluoromethylphenoxy)phenyl | —CO$_2$CH$_3$ | E | viscous liquid |
| 53 | —CH$_3$ | —CH$_3$ | (4-methylthiazol-2-yl)-O-CH(CF$_3$)- | —CO$_2$CH$_3$ | E | $n_D^{25}$ 1.5050 |
| 54 | —CH$_3$ | —CH$_3$ | 3-(4-tert-butylphenoxy)phenyl | —CO$_2$CH$_3$ | E | viscous liquid |

TABLE 1-continued $$\underset{R_1}{\underset{N}{\overset{R_2}{\diagdown}}}\underset{\underset{\underset{OCH_3}{\|}}{CH}}{\overset{OCH_2-A}{\diagdown}}\overset{}{\underset{C-B}{\diagdown}}$$

| Compound No. | $R_1$ | $R_2$ | A | B | isomer* | Physico-chemical properties |
|---|---|---|---|---|---|---|
| 55 | —CH₃ | —CH₃ | 3-methylphenoxy-4-methylphenyl | —CO₂CH₃ | E | viscous liquid |
| 56 | —CH₃ | —CH₃ | 3-methylphenoxy-2,5-dichlorophenyl | —CO₂CH₃ | E | viscous liquid |
| 57 | —CH₃ | —CH₃ | 3-fluorophenyl | —CO₂CH₃ | E | oil |
| 58 | —CH₃ | —CH₃ | 3-bromophenyl | —CO₂CH₃ | E | oil |
| 59 | —CH₃ | —CH₃ | 3-nitrophenyl | —CO₂CH₃ | E | oil |
| 60 | —CH₃ | —CH₃ | 2-naphthyl | —CO₂CH₃ | E | oil |
| 61 | —CH₃ | —CH₃ | 1-naphthyl | —CO₂CH₃ | E | oil |
| 62 | —CH₃ | —CH₃ | 2-benzyloxy-3-methoxy-5-methylphenyl | —CO₂CH₃ | E | viscous liquid |
| 63 | —CH₃ | —CH₃ | 2-fluorenyl | —CO₂CH₃ | E | viscous liquid |

TABLE 1-continued

[Structure: pyrazole with R2, N-N-R1, OCH2-A, and C-B with =CH-OCH3]

| Compound No. | $R_1$ | $R_2$ | A | B | isomer* | Physico-chemical properties |
|---|---|---|---|---|---|---|
| 64 | —CH₃ | —CH₃ | [2-methyl anthraquinone] | —CO₂CH₃ | E | viscous liquid |
| 65 | —CH₃ | —CH₃ | [3-(propargyloxy)phenyl] | —CO₂CH₃ | E | oil |
| 66 | —CH₃ | —CH₃ | [4-(propargyloxy)phenyl] | —CO₂CH₃ | E | oil |
| 67 | —CH₃ | —CH₃ | [3-(trifluoromethoxy)phenyl] | —CO₂CH₃ | E | oil |
| 68 | —CH₃ | —CH₃ | [2-chloro-4,5-dimethylthiazole] | —CO₂CH₃ | E | oil |
| 69 | —CH₃ | —CH₃ | [3,4-diethoxyphenyl] | —CO₂CH₃ | E | oil |
| 70 | —CH₃ | —CH₃ | [3-(2-chlorophenoxy)phenyl] | —CO₂CH₃ | E | viscous liquid |
| 71 | —CH₃ | —CH₃ | [4-benzyloxy-3-methoxyphenyl] | —CO₂CH₃ | E | viscous liquid |
| 72 | —CH₃ | —CH₃ | [4,5-dimethyl-2-phenoxythiazole] | —CO₂CH₃ | E | viscous liquid |

TABLE 1-continued

[Structure: pyrazole with R₂, OCH₂-A, R₁ on N, C-B with =CH-OCH₃]

| Compound No. | R₁ | R₂ | A | B | isomer* | Physico-chemical properties |
|---|---|---|---|---|---|---|
| 73 | —CH₃ | —CH₃ | 2,5-dimethylphenyl | —CO₂CH₃ | E | oil |
| 74 | —CH₃ | —CH₃ | 2-isopropoxy-3-nitrophenyl | —CO₂CH₃ | E | oil |
| 75 | —CH₃ | —CH₃ | 3-isopropoxyphenyl | —CO₂CH₃ | E | oil |
| 76 | —CH₃ | —CH₃ | 2,4-dichlorophenyl | —CO₂CH₃ | E | oil |
| 77 | —CH₃ | —CH₃ | 2-(3-chlorophenoxy)-4,5-dimethylthiazole | —CO₂CH₃ | E | viscous liquid |
| 78 | —CH₃ | —CH₃ | 2-(3-methylphenoxy)-4-chloro-nitrophenyl | —CO₂CH₃ | E | viscous liquid |
| 79 | —CH₃ | —CH₃ | 2,2-dimethylchroman derivative | —CO₂CH₃ | E | viscous liquid |
| 80 | —CH₃ | —CH₃ | chroman derivative | —CO₂CH₃ | E | viscous liquid |

TABLE 1-continued

Structure:
$R_2$ at 3-position, $OCH_2-A$ at 4-position of pyrazole; N-N with $R_1$ on N1; C5 substituent: C(-B)=CH-OCH$_3$

| Compound No. | $R_1$ | $R_2$ | A | B | isomer* | Physico-chemical properties |
|---|---|---|---|---|---|---|
| 81 | —CH$_3$ | —CH$_3$ | 2-Cl, 4-NO$_2$-phenyl | —CO$_2$CH$_3$ | E | viscous liquid |
| 82 | —CH$_3$ | —CH$_3$ | 3-methyl-4-nitro-phenyl, 3-methylphenoxy substituent | —CO$_2$CH$_3$ | E | viscous liquid |
| 83 | —CH$_3$ | —CH$_3$ | 3,4-dimethoxyphenyl | —CO$_2$CH$_3$ | E | oil |
| 84 | —CH$_3$ | —CH$_3$ | 3-OCH$_3$, 4-OC$_2$H$_5$-phenyl | —CO$_2$CH$_3$ | E | oil |
| 85 | —CH$_3$ | —CH$_3$ | 4-benzoylphenyl | —CO$_2$CH$_3$ | E | viscous liquid |
| 86 | —CH$_3$ | —CH$_3$ | 2-nitro-5-methyl-phenyl 3-methylphenoxy substituent | —CO$_2$CH$_3$ | E | viscous liquid |
| 87 | —CH$_3$ | —CH$_3$ | 4,5-dimethyl-thiazol-2-yloxy-(4-chlorophenyl) | —CO$_2$CH$_3$ | E | viscous liquid |
| 88 | —CH$_3$ | —CH$_3$ | methyl-thiazolyloxy-(3-chlorophenyl) | —CO$_2$CH$_3$ | E | viscous liquid |

TABLE 1-continued

[Structure: pyrazole with R2, OCH2-A, R1 on N, C-B with =CH-OCH3]

| Compound No. | R1 | R2 | A | B | isomer* | Physico-chemical properties |
|---|---|---|---|---|---|---|
| 89 | —CH3 | —CH3 | 3-(benzyloxy)phenyl | —CO2CH3 | E | viscous liquid |
| 90 | —CH3 | —CH3 | 2,3,5,6-tetrafluorophenyl | —CO2CH3 | E | oil |
| 91 | —CH3 | —CH3 | 3-(tert-butylcarbonyloxy)phenyl | —CO2CH3 | E | oil |
| 92 | —CH3 | —CH3 | 3-(2-nitro-3-trifluoromethylphenoxy)phenyl | —CO2CH3 | E | viscous liquid |
| 93 | —CH3 | —CH3 | 2,4-dimethylthiazol-5-yl | —CO2CH3 | E | oil |
| 94 | —CH3 | —CH3 | 3-nitro-4-methoxyphenyl | —CO2CH3 | E | oil |
| 95 | —CH3 | —CH3 | 3-methyl-4-(2-nitrophenoxy)phenyl (with additional CH3) | —CO2CH3 | E | viscous liquid |
| 96 | —CH3 | —CH3 | 3-nitro-4-chlorophenyl | —CO2CH3 | E | oil |

TABLE 1-continued

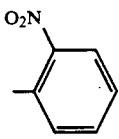

| Compound No. | R₁ | R₂ | A | B | isomer* | Physico-chemical properties |
|---|---|---|---|---|---|---|
| 97 | —CH$_3$ | —CH$_3$ | 2-nitrophenyl | —CO$_2$CH$_3$ | E | oil |
| 98 | —CH$_3$ | —CH$_3$ | 2,4,6-trimethylphenyl | —CO$_2$CH$_3$ | E | oil |
| 99 | —CH$_3$ | —CH$_3$ | 2-methyl-3-nitro-phenyl (with additional methyl) | —CO$_2$CH$_3$ | E | viscous liquid |
| 100 | —CH$_3$ | —CH$_3$ | 3-(2-fluorophenoxy)phenyl | —CO$_2$CH$_3$ | E | viscous liquid |
| 101 | —CH$_3$ | —CH$_3$ | 3-(4-fluorophenoxy)phenyl | —CO$_2$CH$_3$ | E | viscous liquid |
| 102 | —CH$_3$ | —CH$_3$ | 4-methylthiazol-2-yl-O-CH(CF$_3$) | —CO$_2$CH$_3$ | E | viscous liquid |
| 103 | —CH$_3$ | —CH$_3$ | 4-methylthiazol-2-yl-CCl$_2$-(4-methylphenyl) | —CO$_2$CH$_3$ | E | viscous liquid |
| 104 | —CH$_3$ | —CH$_3$ | 4-methylthiazol-2-yl-O-phenyl | —CO$_2$CH$_3$ | E | viscous liquid |

TABLE 1-continued structure at top of table: pyrazole with $R_2$ at 3-position, $OCH_2-A$ at 4-position, $C(=CH-OCH_3)-B$ at 5-position, $R_1$ on N1

| Compound No. | $R_1$ | $R_2$ | A | B | isomer* | Physico-chemical properties |
|---|---|---|---|---|---|---|
| 105 | —$CH_3$ | —$CH_3$ | 3-methylphenyl-O-C(=N-S) (cyclic, benzothiazol-2-yloxy type, oxathiazoline) | —$CO_2CH_3$ | E | viscous liquid |
| 106 | —$CH_3$ | —$CH_3$ | 3-methylphenyl-O-(benzothiazol-2-yl) | —$CO_2CH_3$ | E | oil |
| 107 | —$CH_3$ | —$CH_3$ | benzo[1,3]dioxol-5-yl (methyl-substituted) | —$CO_2CH_3$ | E | viscous liquid |
| 108 | —$CH_3$ | —$CH_3$ | chloro-methyl-benzo[1,3]dioxol-yl | —$CO_2CH_3$ | E | m.p. 137–138° C. |
| 109 | —$CH_3$ | —$CH_3$ | 3-methylphenyl-O-(2-methyl-4-nitrophenyl) | —$CO_2CH_3$ | E | viscous liquid |
| 110 | —$CH_3$ | —$CH_3$ | 3-methylphenyl-O-(2-fluoro-4-nitrophenyl) | —$CO_2CH_3$ | E | viscous liquid |
| 111 | —$CH_3$ | —$CH_3$ | 2-(trifluoromethyl)-methylphenyl | —$CO_2CH_3$ | E | viscous liquid |
| 112 | —$CH_3$ | —$CH_3$ | 3,5-bis(trifluoromethyl)phenyl | —$CO_2CH_3$ | E | viscous liquid |

TABLE 1-continued

[Structure: pyrazole with R₂ at 3-position, N-R₁, with side chain C(=CH-OCH₃)-B and OCH₂-A at 4-position]

| Compound No. | R₁ | R₂ | A | B | isomer* | Physico-chemical properties |
|---|---|---|---|---|---|---|
| 113 | —CH₃ | —CH₃ | 2-methyl-4-chlorophenyl (H₃C, Cl) | —CO₂CH₃ | E | viscous liquid |
| 114 | —CH₃ | —CH₃ | 2-(3-methylphenoxy)-phenyl with NC | —CO₂CH₃ | E | viscous liquid |
| 115 | —CH₃ | —CH₃ | 2-nitro-4-methyl-phenyl-(3-methylphenoxy) (O₂N, CH₃) | —CO₂CH₃ | E | viscous liquid |
| 116 | —CH₃ | —CH₃ | 3-(OCF₂CHF₂)phenyl | —CO₂CH₃ | E | viscous liquid |

*The type of geometrical isomerism of 3-methoxy acrylate or 3-methoxy acrylonitrile group.

TABLE 2

| R₁ | R₂ | A | B |
|---|---|---|---|
| —CH₃ | —CH₃ | 3,5-dichlorophenyl (Cl, Cl) | —CO₂CH₃ |
| —CH₃ | —CH₃ | 4-fluorophenyl (F) | —CO₂CH₃ |
| —CH₃ | —CH₃ | 2,4-dichloro-3,6-difluoro-phenyl (F, Cl, F, Cl) | —CO₂CH₃ |

TABLE 2-continued

| R₁ | R₂ | A | B |
|---|---|---|---|
| —CH₃ | —CH₃ | 4-Br-C₆H₄— | —CO₂CH₃ |
| —CH₃ | —CH₃ | 4-(2-F-C₆H₄-O)-C₆H₄— | —CO₂CH₃ |
| —CH₃ | —CH₃ | 4-(C₆H₅-O)-C₆H₄— | —CN |
| —CH₃ | —CH₃ | 3-(2-CN-C₆H₄-O)-C₆H₄— | —CO₂CH₃ |
| —CH₃ | —CH₃ | 3-(2-NO₂-C₆H₄-O)-C₆H₄— | —CO₂CH₃ |
| —CH₃ | —CH₃ | 4-(2-F-3-CH₃-C₆H₃-O)-C₆H₄— | —CO₂CH₃ |
| —CH₃ | —CH₃ | 4-(2-CF₃-C₆H₄-O)-C₆H₄— | —CO₂CH₃ |
| —CH₃ | —CH₃ | 3-CN-C₆H₄— | —CO₂CH₃ |
| —CH₃ | —CH₃ | 4-NO₂-C₆H₄— | —CO₂CH₃ |
| —C₂H₅ | —CH₃ | 3-(3-CF₃-C₆H₄-O)-C₆H₄— | —CN |

TABLE 2-continued
| R₁ | R₂ | A | B |
|---|---|---|---|
| —CH₃ | -i-C₃H₇ | 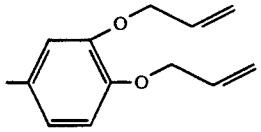 | —CO₂CH₃ |
| -t-C₄H₉ | —CH₃ | 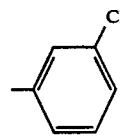 | —CO₂CH₃ |
| —CH₃ | —C₂H₅ | 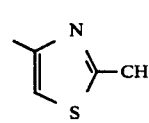 | —CO₂CH₃ |
| —CH₃ | —C₂H₅ | 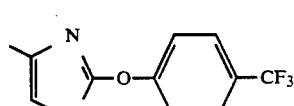 | —CN |
| —CH₃ | -i-C₃H₇ | 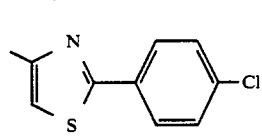 | —CO₂CH₃ |
| —CH₃ | H | 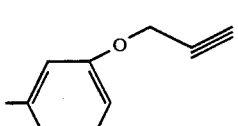 | —CO₂CH₃ |
| —C₂H₅ | H | 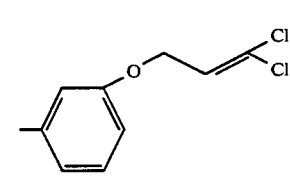 | —CO₂CH₃ |
| CH₃ | H | 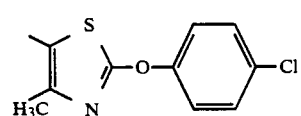 | CO₂CH₃ |
| CH₃ | CH₃ | 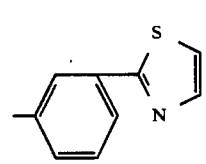 | CO₂CH₃ |
| CH₃ | CH₃ | 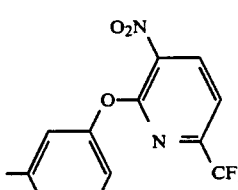 | CO₂CH₃ |
| CH₃ | CH₃ | 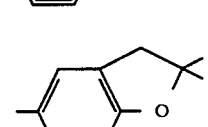 | CO₂CH₃ |

TABLE 2-continued

| $R_1$ | $R_2$ | A | B |
|---|---|---|---|
| $CH_3$ | $CH_3$ | 8-methyl-4,4-dimethylchroman | $CO_2CH_3$ |
| $CH_3$ | $CH_3$ | 2,4-dichloro-methylphenyl | $CO_2CH_3$ |
| H | $CH_3$ | 3-methyl-(4-nitrophenoxy)phenyl | $CO_2CH_3$ |
| $-CH_3$ | $-C_2H_5$ | 4-(prop-2-ynyloxy)methylphenyl | $-CO_2CH_3$ |
| $-CH_3$ | $-CH_3$ | 4-(2,2-dichlorovinyl)methylphenyl | $-CO_2CH_3$ |
| $-CH_3$ | $-CH_3$ | 4-((2-chlorobenzyl)oxy)methylphenyl | $-CO_2CH_3$ |
| $CH_3$ | $CH_3$ | 2-methyl-4-chloro-methylphenyl | $CO_2CH_3$ |

The following Table 3 shows the $^1H$ NMR signals of typical compounds (I) listed in the above Table 1. The chemical shifts are expressed by ppm from tetramethylsilane. Unless otherwise noted, the solvent used is $CDCl_3$.

The abbreviations used are as follows: s=singlet; d=doublet; t=triplet; q=quartet; m=multiplet; br=broad; dd=double doublet.

TABLE 3

| Compound No. | NMR (ppm) |
|---|---|
| 1 | 2.20(3H, s), 3.60(3H, s), 3.75(3H, s), 3.90(3H, s), 4.80(2H, s), 7.4(5H, s), 7.65(1H, s) |
| 2 | 2.15(3H, s), 3.58(3H, s), 3.72(3H, s), 3.87(3H, s), 4.80(2H, s), 6.60(1H, s), 7.37(5H, s) |
| 3 | 2.18(3H, s), 3.58(3H, s), 3.70(3H, s), 3.90(3H, s), 4.80(2H, s), 7.2–7.4(4H, s) 7.62(1H, s) |
| 4 | 2.15(3H, s), 3.58(3H, s), 3.73(3H, s), 3.95(3H, s), 4.79(2H, s), 6.69(1H, s), 7.2–7.45(4H) |
| 5 | 1.30(9H, s), 2.10(3H, s), 3.60(3H, s), 3.75(3H, s), 3.90(3H, s), 4.80(2H, s) 7.35(4H), 7.70(1H, s) |
| 7 | 2.15(3H, s), 3.70(3H, s), 3.88(3H, s), 4.90(2H, s), 7.00(1H, s), 7.4(5H, s) |
| 8 | 2.20(3H, s), 3.80(3H, s), 3.90(3H, s), 4.86(2H, s), 6.92(1H, s), 7.4(5H, s) |
| 9 | 2.18(3H, s), 2.71(3H, s), 3.56(3H, s), 3.72(3H, s), 3.90(3H, s), 4.92(2H, s), 7.05(H, s), 7.64(1H, s) |

TABLE 3-continued

| Compound No. | NMR (ppm) |
|---|---|
| 10 | 2.21(3H, s), 3.59(3H, s), 3.71(3H, s), 3.89(3H, s), 5.05(2H, s), 7.26(1H, s), 7.46(3H, m), 7.68(1H, s), 8.00(2H, m) |
| 12 | 2.13(3H, s), 3.55(3H, s), 3.68(3H, s), 3.83(3H, s), 4.78(2H, s), 6.9~7.2(9H, m), 7.6(1H, s) |
| 13 | 2.11(3H, s), 3.56(3H, s), 3.68(3H, s), 3.89(3H, s), 4.74(2H, s), 6.54(1H, s), 6.9~7.2(9H, m) |
| 14 | 2.13(3H, s), 3.57(3H, s), 3.72(3H, s), 3.89(3H, s), 4.78(2H, s), 6.95–7.38 (9H, m), 7.64(1H, s) |
| 16 | 2.15(3H, s), 3.52(3H, s), 3.70(3H, s), 3.85(3H, s), 4.75(2H, s), 7.15(1H, dd), 7.40(1H, s), 7.45(1H, d), 7.61(1H, s) |
| 17 | 1.22(3H, t), 2.55(2H, q), 3.56(3H, s), 3.69(3H, s), 3.84(3H, s), 4.80(2H, s), 7.31(5H, s), 7.60(1H, s) |
| 18 | 1.23(3H, t), 2.54(2H, q), 3.58(3H, s), 3.72(3H, s), 3.91(3H, s), 4.78(2H, s), 6.64(1H, s), 7.33(5H, s) |
| 19 | 1.25(3H, t), 2.59(2H, q), 3.57(3H, s), 3.70(3H, s), 3.87(3H, s), 4.87(2H, s), 7.4–7.6(4H), 7.61(1H, s) |
| 20 | 1.22(3H, t), 2.53(2H, q), 3.56(3H, s), 3.71(3H, s), 3.85(3H, s), 4.73(2H, s), 5.07(2H, s), 6.9(2H), 7.2(3H), 7.3(4H), 7.60(1H, s) |
| 21 | 1.28(6H, d), 2.96(1H, m), 3.57(3H, s), 3.71(3H, s), 3.85(3H, s), 4.80(2H, s), 7.2–7.35(5H), 7.60(1H, s) |
| 22 | 1.27(6H, d), 2.96(1H, m), 3.59(3H, s), 3.74(3H, s), 3.90(3H, s), 4.77(2H, s), 6.70(1H, s), 7.25–7.4(5H) |
| 23 | 2.16(3H, s), 2.35(3H, s), 3.56(3H, s), 3.71(3H, s), 3.86(3H, s), 4.78(2H, s), 7.05–7.3(4H), 7.61(1H, s) |
| 24 | 2.16(3H, s), 2.35(3H, s), 3.57(3H, s), 3.71(3H, s), 3.90(3H, s), 4.75(2H, s), 6.61(1H, s), 7.06–7.3(4H) |
| 25 | 2.17(3H, s), 3.56(3H, s), 3.70(3H, s), 3.87(3H, s), 4.89(2H, s), 7.0–7.15(2H), 7.25–7.4(2H), 7.62(1H, s) |
| 26 | 2.20(3H, s), 3.56(3H, s), 3.68(3H, s), 3.86(3H, s), 4.94(2H, s), 7.24–7.52(4H), 7.61(1H, s) |
| 27 | 2.17(3H, s), 3.56(3H, s), 3.70(3H, s), 3.87(3H, s), 4.88(2H, s), 7.40–7.60(4H), 7.61(1H, s) |
| 28 | 2.17(3H, s), 3.56(3H, s), 3.69(3H, s), 3.85(3H, s), 4.88(2H, s), 7.42(2H, d), 7.56(2H, d), 7.59(2H, d) |
| 29 | 2.17(3H, s), 3.56(3H, s), 3.70(3H, s), 3.80(3H, s), 3.86(3H, s), 4.80(2H, s), 6.8–6.9(3H), 7.24(1H, d), 7.61(1H, s) |
| 30 | 2.14(3H, s), 3.55(3H, s), 3.70(3H, s), 3.86(3H, s), 4.78(2H, s), 7.2–7.3 (4H, m), 7.61(H, s) |
| 31 | 2.12(3H, s), 3.56(3H, s), 3.70(3H, s), 3.91(3H, s), 4.74(2H, s), 6.58(H, s), 7.2–7.4(4H, m) |
| 32 | 1.31(3H, t), 2.15(3H, s), 3.70(3H, s), 3.80(2H, q), 3.86(3H, s), 4.82(2H, s), 7.26–7.35(5H), 7.62(H, s) |
| 33 | 1.32(3H, t), 2.15(3H, s), 3.70(3H, s), 3.82(2H, q), 3.89(3H, s), 4.79(2H, s), 6.56(H, s), 7.30–7.37(5H) |
| 34 | 1.31(3H, t), 2.18(3H, s), 3.71(3H, s), 3.80(2H, q), 3.85(3H, s), 4.80(2H, s), 7.18–7.34(4H), 7.61(1H, s) |
| 35 | 1.31(3H, t), 2.14(3H, s), 3.67(3H, s), 3.80(2H, q), 3.82(3H, s), 4.78(2H, s), 6.92–7.34(9H), 7.61(1H, s) |
| 36 | 2.15(3H, s), 2.25(3H, s), 2.27(3H, s), 3.55(3H, s), 3.70(3H, s), 3.86(3H, s), 4.75(2H, s), 7.10(3H, m), 7.62(H, s) |
| 37 | 2.1(3H, s), 3.6(3H, s), 3.7(3H, s), 3.9(3H, s), 4.8(2H, s), 7.0–7.6(8H, m), 7.6(H, s) |
| 38 | 2.14(3H, s), 3.55(3H, s), 3.68(3H, s), 3.83(3H, s), 4.84(2H, s), 7.0–7.2(6H), 7.60(H, s), 7.82(H, t) |
| 39 | 2.15(3H, s), 3.55(3H, s), 3.71(3H, s), 3.89(3H, s), 4.84(2H, s), 7.41–7.63 (5H) |
| 40 | 2.13(3H, s), 3.55(3H, s), 3.68(3H, s) 3.85(3H, s), 4.81(2H, s), 6.8–7.5 (8H, m), 7.61(1H, s) |
| 41 | 2.2(3H, s), 3.6(3H, s), 3.7(3H, s), 3.9(3H, s), 4.8(2H(2H, s), 6.9–7.6(8H, m) |
| 42 | 2.2(3H, s), 2.3(6H, s), 3.6(3H, s), 3.7(3H, s), 3.9(3H, s), 4.8(2H, s), 7.0–7.1(3H), 7.6(H, s) |
| 43 | 2.1(3H, s), 3.6(3H, s), 3.7(3H, s), 3.9(3H, s), 4.8(2H, s), 6.9–8.2(9H, s) |
| 44 | 2.2(3H, s), 3.5(3H, s), 3.7(3H, s), 3.9(3H, s), 4.7(1H, d), 4.8(2H, s), 6.2(1H, t), 6.8–7.3(4H), 7.6(1H, s) |
| 45 | 2.16(3H, s), 3.56(3H, s), 3.70(3H, s), 3.87(3H, s), 4.86(2H, s), 7.1(H, dd), 7.18(H, dd), 7.22(H, dd), 7.4(H, dd), 7.61(H, s), 7.99(H, d), 8.24(H, d) |
| 46 | 2.20(3H, s), 3.56(3H, s), 3.69(3H, s), 3.97(3H, s), 4.81(2H, s), 7.10–7.40 (3H), 7.60(1H, s) |
| 47 | 2.12(3H, s), 3.55(3H, s), 3.68(3H, s), 3.81(3H, s), 3.84(3H, s), 4.76(2H, s), 6.8–7.4(8H, m), 7.60(1H, s) |
| 48 | 2.11(3H, s), 3.56(3H, s), 3.68(3H, s), 3.85(3H, s), 4.78(2H, s), 6.9–7.35 (8H, m), 7.61(1H, s) |
| 49 | 2.13(3H, s), 3.56(3H, s), 3.69(3H, s), 3.86(3H, s), 4.80(2H, s), 6.8–7.4 (7H, m), 7.62(1H, s) |
| 50 | 2.2(3H, s), 3.6(3H, s), 3.7(3H, s), 3.8(3H, s), 4.8(2H, s), 7.0–7.6(9H, m) |
| 51 | 2.1(3H, s), 3.5(3H, s), 3.7(3H, s), 3.9(3H, s), 4.8(2H, s), 6.9–8.0(9H, m) |
| 52 | 2.1(3H, s), 3.5(3H, s), 3.7(3H, s) 3.8(3H, s), 4.8(2H, s), 6.9–7.7(8H, m) |
| 53 | 1.5(3H, d), 2.1(3H, s), 3.5(3H, s), 3.7(3H, s), 3.9(3H, s), 4.8(2H, s), 5.5(1H, m), 6.9(1H, s), 7.6(1H, s) |
| 54 | 1.56(9H, s), 2.12(3H, s), 3.56(3H, s), 3.68(3H, s), 3.83(3H, s), 4.78(2H, s), 6.9–7.4(8H, m), 7.60(1H, s) |
| 55 | 2.12(3H, s), 2.34(3H, s), 3.55(3H, s), 3.68(3H, s), 3.84(3H, s), 4.77(2H, s), 6.9–7.3(8H, m), 7.6(1H, s) |
| 56 | 2.16(3H, s), 3.56(3H, s), 3.69(3H, s), 3.86(3H, s), 4.82(2H, s), 6.8–7.4(7H, m), 7.62(1H, s) |
| 57 | 2.18(3H, s), 3.57(3H, s), 3.71(3H, s), 3.88(3H, s), 4.82(2H, s), 6.9–7.1(3H, m), 7.2–7.4(1H, m), 7.61(1H, s) |
| 58 | 2.18(3H, s), 3.57(3H, s), 3.71(3H, s), 3.88(3H, s), 4.82(2H, s), 6.9–7.1(3H, m), 7.2–7.4(1H, m), 7.61(1H, s) |
| 59 | 2.20(3H, s), 3.57(3H, s), 3.70(3H, s), 3.91(3H, s), 4.93(1H, s), 7.51(1H, t), 7.64(1H, s), 7.64(1H, dd), 8.18(1H, dd), 8.23(1H, d) |
| 60 | 2.20(3H, s), 3.54(3H, s), 3.60(3H, s), 3.73(3H, s), 4.99(2H, s), 7.5(4H), 7.73(H, s), 7.8(3H) |
| 61 | 2.13(3H, s) 3.52(3H, s), 3.63(3H, s), 3.76(3H, s), 5.27(2H, s), 7.36(3H, s), 7.37(2H), 7.5(2H), 7.8(2H), 8.19(H), |
| 62 | 2.08(3H, s), 3.53(3H, s), 3.70(3H, s), 3.83(3H, s), 3.88(3H, s), 4.69(2H, s), 5.13(2H, s), 6.8–6.9(3H), 7.3–7.5(5H), 7.60(H, s) |
| 63 | 2.17(3H, s), 3.57(3H, s), 3.67(3H, s), 3.83(3H, s), 3.90(2H, s), 4.86(2H, s), 7.2–7.4(3H), 7.5–7.6(2H), 7.59(H, s), 7.7–7.8(2H, m) |
| 64 | 2.31(3H, s), 3.57(3H, s), 3.69(3H, s), 3.93(3H, s), 500(2H, s), 7.64(1H, s), 7.75–7.85(3H, m), 8.28–8.35(4H, m) |
| 65 | 2.15(3H, s), 2.52(1H, t), 3.56(3H, s), 3.71(3H, s), 3.87(3H, s), 4.69(2H, d), 4.80(2H, s), 6.90–6.96(3H), 7.26(1H, |

TABLE 3-continued

| Compound No. | NMR (ppm) |
|---|---|
| | 7.61(1H, s) |
| 66 | 2.11(3H, s), 2.52(1H, t), 3.56(3H, s), 3.71(3H, s), 3.87(3H, s), 4.69(2H, d), 4.75(2H, d), 6.93(2H, d), 7.25(2H, d), 7.62(1H, s) |
| 68 | 2.18(3H, s), 2.34(3H, s), 3.57(3H, s), 3.74(3H, s), 3.92(3H, s), 4.85(2H, s), 7.62(H, s) |
| 69 | 1.44(3H, t), 2.11(3H, s), 3.56(3H, s), 3.72(3H, s), 3.87(3H, s), 4.1–4.2 (4H, m), 4.72(2H, s), 6.75–6.9(3H), 7.62(H, s) |
| 70 | 2.13(3H, s), 3.57(3H, s), 3.69(3H, s), 3.86(3H, s), 4.79(2H, s), 6.8–7.4(7H, m), 7.47(1H, dd), 7.61(1H, s) |
| 71 | 2.12(3H, s), 3.56(3H, s), 3.70(3H, s), 3.84(3H, s), 3.89(3H, s), 4.73(2H, s), 5.16(2H, s), 6.7–6.9(3H, m), 7.2–7.5 (5H, m), 7.59(1H, s) |
| 72 | 2.14(3H, s), 2.17(3H, s), 3.56(3H, s), 3.71(3H, s), 3.88(3H, s), 4.78(2H, s), 7.27(1H, s), 7.4(2H), 7.62(H, s) |
| 73 | 2.13(3H, s), 2.41(3H, s), 3.55(3H, s), 3.69(3H, s), 3.85(3H, s), 4.80(2H, s), 6.93(2H, dd), 7.00(1H, t), 7.11(1H, d), 7.27–7.34(2H, m), 7.61(1H, s), 7.76(1H, d) |
| 74 | 1.39(3H, d), 2.16(3H, s), 3.56(3H, s), 3.72(3H, s), 3.90(3H, s), 4.65(H, m), 4.78(2H, s), 7.03(H, d), 7.43(H, dd), 7.63(H, s), 7.76(H, d) |
| 75 | 1.32(6H, d), 2.19(3H, s), 3.56(3H, s), 3.71(3H, s), 3.87(3H, s), 4.54(1H, quint), 4.77(2H, s), 6.78–6.89(3H, m), 7.21(1H, t), 7.62(1H, s), |
| 76 | 2.24(3H, s), 3.56(3H, s), 3.70(3H, s), 3.88(3H, s), 4.91(2H, s), 7.18–7.30(2H), 7.51(1H, d), 7.61(1H, s) |
| 77 | 2.14(3H, s), 2.78(3H, s), 3.57(3H, s), 3.73(3H, s), 3.90(3H, s), 4.80(2H, s), 7.17–7.36(4H, m), 7.64(1H, s) |
| 78 | 2.17(3H, s), 3.56(3H, s), 3.70(3H, s), 3.87(3H, s), 4.48(2H, s), 6.95–7.42 (7H, m), 7.62(1H, s), 7.94(1H, s) |
| 79 | 1.47(6H, s), 2.13(3H, s), 3.00(2H, s), 3.56(3H, s), 3.74(3H, s), 3.88(3H, s), 4.70(2H, s), 6.66(1H, d), 7.02(1H, s), 7.12(1H, s), 7.63(1H, s) |
| 80 | 1.32(6H, s), 1.82(2H, dd), 2.06(3H, s), 3.57(3H, s), 3.73(3H, s), 3.89(3H, s), 4.17(2H, dd), 4.70(2H, s), 6.72(1H, d), 6.98(1H, dd), 7.21(1H, s), 7.67(1H, s) |
| 81 | 2.19(3H, s), 3.55(3H, s), 3.71(3H, s), 3.81(3H, s), 4.12(1H, q), 4.87(2H, s), 7.42–7.53(2H, m), 7.62(1H, s), 7.89 (1H, d) |
| 83 | 2.13(3H, s), 3.56(3H, s), 3.71(3H, s), 3.87(9H, d), 4.75(2H, s), 6.81(2H, s), 6.88(1H, s), 7.61(1H, s) |
| 84 | 1.46(3H, t), 2.11(3H, s), 3.56(3H, s), 3.71(3H, s), 3.86(3H, s), 3.87(3H, s), 4.09(2H, q), 6.81(2H, s), 6.87(1H, s), 7.62(1H, s) |
| 85 | 2.10(3H, s), 3.57(3H, s), 3.71(3H, s), 3.88(3H, s), 4.92(2H, s), 7.44–7.81 (10H, m) |
| 87 | 2.14(3H, s), 2.17(3H, s), 3.56(3H, s), 3.72(3H, s), 3.90(3H, s), 4.79(2H, s), 7.23(2H, d), 7.37(2H, d), 7.63(H, s) |
| 88 | 2.20(3H, s), 3.57(3H, s), 3.71(3H, s), 3.87(3H, s), 4.77(2H, s), 6.78(H, s), 7.2–7.4(4H), 7.64(H, s) |
| 89 | 2.16(3H, s), 3.59(3H, s), 3.69(3H, s), 3.84(3H, s), 4.79(2H, s), 5.06(2H, s), 6.85–7.00(3H), 7.20–7.46(6H), 7.60 (1H, s) |
| 90 | 2.24(3H, s), 3.56(3H, s), 3.62(3H, s), 3.85(3H, s), 4.77(2H, s), 7.54(1H, s), |
| 91 | 1.36(9H, s), 3.17(3H, s), 3.56(3H, s), |
| | 3.71(3H, s), 3.85(3H, s), 4.83(2H, s), 6.98(H, dd), 7.06(H, d), 7.18(H, d), 7.33(H, dd), 7.61(H, s) |
| 93 | 2.14(3H, s), 2.35(3H, s), 3.57(3H, s), 3.73(3H, s), 3.90(3H, s), 4.95(3H, s), 4.95(2H, s), 7.61(1H, s), 8.68(H, s) |
| 94 | 2.16(3H, s), 3.56(3H, s), 3.71(3H, s), 3.91(3H, s), 3.97(3H, s), 4.80(1H, s), 7.04(H, d), 7.48(H, dd), 7.64(H, s), 7.84(H, d) |
| 96 | 2.50(3H, s), 3.57(3H, s), 3.69(3H, s), 3.92(3H, s), 5.00(2H, s), 7.52(1H, d), 7.64(1H, s), 8.13(1H, dd), 8.44(1H, d) |
| 97 | 2.23(3H, s), 3.56(3H, s), 3.67(3H, s), 3.87(3H, s), 5.27(2H, t), 7.46(1H, t), 7.62(1H, s), 7.67(1H, s), 7.91(1H, d) 8.10(1H, d) |
| 98 | 2.18(3H, s), 2.26(3H, s), 2.32(6H, s), 3.56(3H, s), 3.70(3H, s), 3.87(3H, s), 4.82(2H, s), 6.83(2H, s), 7.61(1H, s) |
| 99 | 2.16(3H, s), 3.55(3H, s), 3.70(3H, s), 3.87(3H, s), 4.90(2H, s), 7.27(1H, t), 7.49(1H, d), 7.58(1H, s), 7.72(1H, d) |
| 100 | 2.13(3H, s), 3.55(3H, s), 3.69(3H, s), 3.84(3H, s), 4.79(2H, s), 6.88–7.30 (8H, m), 7.60(1H, s) |
| 101 | 2.12(3H, s), 3.56(3H, s), 3.68(3H, s), 3.85(3H, s), 4.78(2H, s), 6.84–7.08 (7H, m), 7.28(1H, t), 7.61(1H, s) |
| 102 | 1.56(3H, d) 2.62(3H, s) 3.57(3H, s) 3.71(3H, s) 3.89(3H, s) 4.71(2H, s) 5.60(1H, quint) 6.61(1H, s) 7.64(1H, s) |
| 103 | 2.19(3H, s) 2.45(3H, s) 3.57(3H, s) 3.73(3H, s) 3.91(3H, s) 5.09(2H, s) 7.32(2H, dd) 7.64(1H, s) 7.86(1H, s) 8.37(1H, dd) |
| 104 | 2.17(3H, s) 3.55(3H, s) 3.69(3H, s) 3.85(3H, s) 4.87(1H, s) 7.24–7.45(4H, m) 7.62(1H, s) 7.65–7.75(2H, m) |
| 105 | 2.16(3H, s) 3.56(3H, s) 3.70(3H, s) 3.86(3H, s) 4.84(2H, s) 6.83(1H, d) 7.10–7.40(5H, m) 7.62(1H, s) |
| 106 | 2.20(3H, s) 3.57(3H, s) 3.71(3H, s) 3.86(3H, s) 4.78(2H. s) 6.73(1H, s) 7.20–7.32(4H, m) 7.38–7.45(2H, m) 7.63(1H, s) |
| 107 | 2.14(3H, s), 3.72(3H, s), 3.80(3H, s), 4.70(2H, s), 5.95(2H, s), 6.75(2H, s), 6.83(1H, s), 7.63(1H, s) |
| 108 | 2.20(3H, s), 3.56(3H, s), 3.71(3H, s), 3.98(3H, s), 4.83(2H, s), 5.97(2H, s), 6.82(1H, s), 6.91(1H, s), 7.63(1H, s) |
| 109 | 2.13(3H, s), 2.41(3H, s), 3.56(3H, s), 3.68(3H, s), 3.86(3H, s), 4.82(2H, s), 6.77(1H, d), 6.93(1H, dd), 7.02(1H, d), 7.18(1H, d), 7.37(1H, t), 7.62(1H, s), 8.00(1H, dd), 8.16(1H, d) |
| 110 | 2.12(3H, s), 3.55(3H, s), 3.69(3H, s), 3.86(3H, s), 4.83(2H, s), 6.91–7.08(3H, m), 7.21(1H, d), 7.39(1H, d), 7.62(1H, s), 7.99(1H, s), 8.08(1H, dd) |
| 111 | 2.11(3H, s), 3.58(3H, s), 3.69(3H, s), 3.86(3H, s), 5.04(2H, s), 7.39(1H, t), 7.55(1H, t), 7.63(1H, d), 7.64(1H, s), 7.76(1H, d) |
| 112 | 2.21(3H, s), 3.58(3H, s), 3.88(3H, s), 4.95(2H, s), 7.62(1H, s), 7.81(3H, s) |
| 115 | 2.13(3H, s), 2.30(3H, s), 2.33(3H, s), 3.56(3H, s), 3.70(3H, s), 3.86(3H, s), 4.78(2H, s), 6.95(H, d), 6.98(H, s), 7.10(H, d), 7.60(H, s) |
| 116 | 2.15(3H, s), 3.56(3H, s), 3.71(3H, s), 3.87(3H, s), 4.83(2H, s), 5.91(1H, m), 7.16–7.38(4H, m), 7.62(1H, s) |

TABLE 4

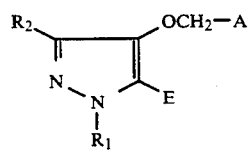

| intermediate | R₁ | R₂ | E | A | NMR (ppm) |
|---|---|---|---|---|---|
| a | $-CH_3$ | $-CH_3$ | $-CO_2C_2H_5$ | 4-phenoxyphenyl | 1.35(3H, t), 2.01(3H, s), 4.0(3H, s), 4.3(2H, q), 4.85(2H, s), 6.9–7.5(9H) |
| b | $-CH_3$ | $-CH_3$ | $-CO_2C_2H_5$ | 3-phenoxyphenyl | 1.3(3H, t), 2.05(3H, s), 4.0(3H, s), 4.28(2H, q), 4.88(2H, s), 6.9–7.4(9H) |
| c | $-CH_3$ | $-C_2H_5$ | $-CO_2C_2H_5$ | phenyl | 1.2(3H, t), 1.4(3H, t), 2.5(2H, q), 4.1(3H, s), 4.4(3H, q), 5.0(2H, s), 7.3–7.5(5H) |
| d | $-CH_3$ | $-CH_3$ | $-CO_2C_2H_5$ | 3-methylphenyl | 1.35(3H, t), 2.1(3H, s), 2.35(2H, q), 4.06(3H, s), 4.36(3H, q), 4.94(2H, s), 7.1–7.4(4H) |
| e | $-CH_3$ | $-CH_3$ | $-CO_2C_2H_5$ | 4-chlorophenyl | 1.35(3H, t), 2.05(3H, s), 4.05(3H, s), 4.35(2H, q), 4.93(2H, s), 7.34(4H) |
| f | $-CH_3$ | $-CH_3$ | $-CO_2C_2H_5$ | 3-chlorophenyl | 1.32(3H, t), 2.10(3H, s), 4.02(3H, q), 4.35(2H, q), 4.92(2H, q), 7.3–7.5(4H) |
| g | $-CH_3$ | $-CH_3$ | $-CO_2C_2H_5$ | 2,4-dichlorophenyl | 1.30(3H, t), 2.12(3H, s), 4.05(3H, s), 4.34(2H, q), 5.04(2H, s), 7.29(H, dd), 7.41(H, d), 7.55(H, d) |
| h | $-CH_3$ | $-C_2H_5$ | $-CH_2CN$ | phenyl | 1.3(3H, t), 2.65(2H, q), 3.35(2H, s), 3.8(3H, s), 4.9(2H, s), 7.4–7.3(5H) |
| i | $-CH_3$ | $-CH_3$ | $-CH_2CN$ | 3-methylphenyl | 2.2(3H, s), 2.4(3H, s), 3.42(3H, s), 3.8(3H, s), 4.85(2H, s), 7.2–7.4(4H) |
| j | $-CH_3$ | $-CH_3$ | $-CH_2CN$ | 4-chlorophenyl | 2.18(3H, s), 3.4(2H, s), 3.78(3H, s), 4.8(2H, s), 7.28(2H, d), 7.35(2H, d) |

TABLE 4-continued $$\underset{R_1}{\underset{|}{N}}\underset{N}{\overset{R_2}{\diagup}}\underset{E}{\overset{OCH_2-A}{\diagdown}}$$

| intermediate | $R_1$ | $R_2$ | E | A | NMR (ppm) |
|---|---|---|---|---|---|
| k | —CH₃ | —CH₃ | —CH₂CN | 3-chlorophenyl | 2.12(3H, s), 3.45(3H, s), 3.78(3H, s), 4.83(2H, s), 7.2–7.4(4H). |
| l | —CH₃ | —CH₃ | —CH₂CN | 2,4-dichlorophenyl | 2.20(3H, s), 3.56(2H, s), 3.79(3H, s), 4.94(2H, s), 7.28(H, dd), 7.39(H, d), 7.46(H, d) |
| m | —CH₃ | —CH₃ | —CH₂CO₂CH₃ | 3-phenoxyphenyl | 2.13(3H, s), 3.50(2H, s), 3.67(3H, s), 3.68(3H, s), 4.80(2H, s), 6.9–7.4(9H) |
| n | —CH₃ | —C₂H₅ | —CH₂CO₂CH₃ | phenyl | 1.25(3H, t), 2.55(2H, q), 3.5(2H, s), 3.72(3H, s), 4.85(2H, s), 7.4–7.5(5H) |
| o | —CH₃ | —CH₃ | —CH₂CO₂CH₃ | 3-methylphenyl | 2.15(3H, s), 2.36(3H, s), 3.49(2H, s), 3.68(6H, s), 4.79(2H, s), 7.1–7.25(4H) |
| p | —CH₃ | —CH₃ | —CH₂CO₂CH₃ | 4-chlorophenyl | 2.13(3H, s), 3.47(2H, s), 3.69(6H, s), 4.79(2H, s), 7.2–7.4(4H) |
| q | —CH₃ | —CH₃ | —CH₂CO₂CH₃ | 4-chloropyridin-2-yl | 2.15(3H, s), 3.51(2H, s), 3.69(3H, s), 3.70(3H, s), 4.81(2H, s), 7.2–7.4(4H) |
| r | —CH₃ | —CH₃ | —CH₂CO₂CH₃ | 2,4-dichlorophenyl | 2.16(3H, s), 3.56(2H, s), 3.69(3H, s), 3.70(3H, s), 4.91(2H, s), 7.26(H, dd), 7.44(H, d), 7.43(H, d) |

The following formulation examples are illustrative only and are not intended to limit the scope of the invention in any way.

FORMULATION 1

A wettable powder was prepared using the following ingredients:

| | Quantity parts by weight |
|---|---|
| Active compound (No. 1 in the Table 1) | 20 |
| diatomaceous earth | 75 |
| surfactant | 5 |
| (principal component = alkylbenzene sulfonate) | |

The above ingredients are mixed and ground into a homogeneous powder.

FORMULATION 2

A wettable powder was prepared using the following ingredients:

|  | Quantity parts by weight |
|---|---|
| Active compound (No. 10 in the Table 1) | 40 |
| white carbon | 10 |
| diatomaceous earth | 47 |
| "Sorpol" 5039 | 3 |
| (surfactant from TOHO Chemicals, Inc.: principal component = polyoxyethylene alkylaryl ether sulfonate) | |

The above ingredients are mixed and ground into a homogeneous powder.

FORMULATION 3

An emulsifiable concentrated formulation was prepared using the following ingredients:

|  | Quantity parts by weight |
|---|---|
| Active compound (No. 15 in the Table 1) | 30 |
| "Sorpol" 3005X | 15 |
| (TOHO Chemicals, Inc.: nonionic/anionic surfactant blend) | |
| xylene | 25 |
| dimethylformamide | 30 |

The above ingredients are mixed to obtain an emulsifiable concentrated formulation which gives emulsion upon dilution with water.

FORMULATION 4

A dust was prepared using the following ingredients:

|  | Quantity parts by weight |
|---|---|
| Active compound (No. 1 in the Table 1) | 2 |
| N,N-kaolin clay (TSUCHIYA KAOLIN, Inc.) | 98 |

The above ingredients are intimately mixed and ground to obtain a dust.

The following Tests were performed to demonstrate the ability of the compounds of the invention to effect bactericidal and fungicidal action and to evaluate their agricultural- and horticultural-usefulness.

In the Tests, the compounds of the invention are shown by the Nos. in the Table 1, while the control compounds are shown by the simboles used in the following Table 5.

TABLE 5

| Compound No. | Structure | Reference |
|---|---|---|
| A | [structure] | Japanese Patent Publication (kokai) No. 277652/1986 |
| B | [structure] | European Patent Publication No. 178826 |
| C | [structure] | Japanese Patent Publication (kokai) No. 254669/1989 |

TEST 1

Evaluation of Efficacy of the compound (I) on the Control of Wheat Powdery Mildew A wettable powder containing the test compound was prepared in the same manner as previously described in the Formulation 1 and diluted with water to obtain a test solution containing the test compound at a given concentration. The test solution was then applied to a wheat (variety: Norin No. 61; 1- or 2-leaf-stage) growing in a pot (6 cm in diameter) by stem-foliar application at the application rate of 10 ml per pot. After the test solution was air-dried, the plant was inoculated with *Erysiphe graminis* f. sp. tritici. The inoculation was conducted by spraying a suspension of spores collected from leaves of wheat infected with powdery mildew. The treated plants were maintained in a green house for 7 to 10 days and the portion of diseased area on leaves of each plant was measured.

The disease control value was calculated as prevention value from the equation:

$$\text{prevention value } (\%) = [(A - B)/A] \times 100$$

where A is the mean value of the percent of diseased area on untreated sections, B is the mean value of the percent of diseased area on treated sections. Results are shown in the following Table 6.

TABLE 6

| Compound No. | Concentration of active ingredient (ppm) | Prevention value (%) |
|---|---|---|
| 1 | 200 | 100 |
| 2 | 200 | 95 |
| 3 | 200 | 100 |
| 4 | 200 | 96 |
| 5 | 200 | 80 |
| 10 | 200 | 77 |
| 12 | 200 | 95 |
| 14 | 200 | 100 |
| 16 | 200 | 97 |
| 17 | 200 | 99 |
| 18 | 200 | 90 |
| 19 | 200 | 99 |
| 20 | 200 | 78 |
| 21 | 200 | 75 |

TABLE 6-continued

| Compound No. | Concentration of active ingredient (ppm) | Prevention value (%) |
|---|---|---|
| 23 | 200 | 100 |
| 24 | 200 | 93 |
| 25 | 200 | 100 |
| 26 | 200 | 100 |
| 27 | 200 | 100 |
| 28 | 200 | 100 |
| 29 | 200 | 100 |
| 30 | 200 | 100 |
| 31 | 200 | 95 |
| 32 | 200 | 100 |
| 34 | 200 | 99 |
| 35 | 200 | 90 |
| 36 | 200 | 99 |
| 40 | 200 | 99 |
| 41 | 200 | 94 |
| 42 | 200 | 100 |
| 43 | 200 | 95 |
| 44 | 200 | 96 |
| 45 | 200 | 100 |
| 46 | 200 | 100 |
| 48 | 200 | 95 |
| 49 | 200 | 96 |
| 50 | 200 | 96 |
| 52 | 200 | 97 |
| 53 | 200 | 93 |
| 55 | 200 | 99 |
| 56 | 200 | 100 |
| 57 | 200 | 97 |
| 58 | 200 | 100 |
| A | 200 | 0 |
| B | 200 | 12 |

TEST 2

Evaluation of Efficacy of the compound (I) on the Control of Wheat Powdery Mildew (Systemic Activity Test)

A wettable powder containing a test compound was prepared in the same manner as previously described in the Formulation 1 and diluted with water to obtain a test solution containing the test compound at a given concentration. Wheat seedlings (variety: Norin No. 61; 1- or 2-leaf-stage) were treated by immersing the roots into the test solution. Two days later, the seedlings were inoculated with *Erysiphe graminis* f. sp. tritici. The inoculation was conducted by spaying suspensions of spores collected from leaves of wheats infected with *E. graminis* f. sp. tritici. The treated plants were kept at room temperature for 7 to 10 days and the portion of diseased spot areas on leaves of each plant was measured.

The disease control value was circulated as percent control from the equation:

prevention value (%) = $[(A-B)/A] \times 100$ where A is the mean value (%) of the percent diseased area on untreated sections, B is the mean value (%) of the percent diseased area on treated sections. Results are shown in the following Table 7.

TABLE 7

| Compound No. | Concentration of active ingredient (ppm) | Prevention value (%) |
|---|---|---|
| 1 | 50 | 100 |
|  | 5 | 100 |
| 3 | 50 | 100 |
|  | 5 | 100 |
| 12 | 50 | 100 |
|  | 5 | 100 |
| 16 | 50 | 100 |
|  | 5 | 100 |
| 19 | 50 | 100 |

TABLE 7-continued

| Compound No. | Concentration of active ingredient (ppm) | Prevention value (%) |
|---|---|---|
|  | 5 | 100 |
| 23 | 50 | 100 |
|  | 5 | 100 |
| 25 | 50 | 100 |
|  | 5 | 100 |
| 30 | 50 | 100 |
|  | 5 | 100 |
| 33 | 50 | 100 |
|  | 5 | 100 |
| 36 | 50 | 100 |
|  | 5 | 100 |
| 42 | 50 | 100 |
|  | 5 | 100 |
| 45 | 50 | 100 |
|  | 5 | 100 |
| 46 | 50 | 100 |
|  | 5 | 100 |
| 56 | 50 | 100 |
|  | 5 | 100 |
| A | 50 | 0 |
|  | 5 | 0 |
| B | 50 | 34 |
|  | 5 | 0 |

TEST 3

Evaluation of Efficacy of the Compound (I) on the Control of Wheat Leaf Rust

A wettable powder containing a test compound was prepared in the same manner as previously described in the Formulation 1 and diluted with water to obtain a test solution containing the test compound at a given concentration. The test solution was then applied to a wheat seedlings (variety: Norin No. 61; 1- or 2-leaf-stage) growing in a pot (6 cm in diameter) by stem-foliar application at the application rate of 10 ml per pot. After the test solution was air-dried, the seedlings was inoculated with *Puccina recondita*. The inoculationi was conducted by spraying a suspension of spores collected by grinding wheat leaves infected with leaf rust. The inoculated plants were kept, at first, in a wet chamber at 22° C. for 15 hours, and then in a green house for 7 days. The portion of diseased area of each leaf was measured.

The disease control value was calculated as percent control from the equation:

prevention value (%) = $[(A-B)/A] \times 100$ where A is the mean value (%) of the percent diseased area on untrated sections, B is the mean value (%) of the percent injured area on treated sections. Results are shown in the following Table 8.

TABLE 8

| Compound No. | Concentration of active ingredient (ppm) | Prevention value (%) |
|---|---|---|
| 1 | 200 | 95 |
| 2 | 200 | 80 |
| 3 | 200 | 100 |
| 4 | 200 | 95 |
| 5 | 200 | 100 |
| 12 | 200 | 100 |
| 14 | 200 | 100 |
| 16 | 200 | 100 |
| 26 | 200 | 100 |
| 35 | 200 | 100 |
| 42 | 200 | 99 |
| 77 | 200 | 100 |
| 78 | 200 | 100 |
| A | 200 | 0 |

TABLE 8-continued

| Compound No. | Concentration of active ingredient (ppm) | Prevention value (%) |
|---|---|---|
| C | 200 | 5 |

TEST 4

Evaluation of Efficacy of the Compound (I) on the Control of Late Blight of Tomato A wettable powder containing a test compound was prepared in the same manner as previously described in the Formulation 1 and diluted with water to obtain a test solution containing the test compound at a given concentration. Three seedlings of tomato (variety: Red cherry) were grown in a plastic pot (6 cm in diameter) until 3- or 4-leaf-stage. The test solution was applied to the seedlings by stem-foliar application at the application rate of 10 ml per pot. After the test solution was air-dried, the seedlings were inoculated with *Phytophthora infestans*. The inoculation was conducted by spraying a suspension of spores formed on detached leaves of tomato. The inoculated plants were kept, at first, in a wet chamber at 20° C. for 24 hours, and then in a green house for 2 days. The portion of diseased areas of the leaves was measured. The incidence of disease was rated using the following index:

| index | spot area |
|---|---|
| 0 | none |
| 1 | less than 1/8 |
| 3 | 1/8 to 3/8 |
| 5 | more than 3/8 |

The incidence of disease (%) was calculated from the equation:

$$\frac{0 \times n_0 + 1 \times n_1 + 3 \times n_3 + 5 \times n_5}{5(n_0 + n_1 + n_3 + n_5)} \times 100$$

where $n_0$, $n_1$, $n_3$, and $n_5$ are the number of leaves which give the index listed above per pot.

The disease control value was calculated as percent control from the equation:

prevention value (%) = [(A − B)/A] × 100 where A is the incidence (%) of disease on untreated sections, B is the incidence (%) of disease on treated sections. Results are shown in the following Table 9.

TABLE 9

| Compound No. | Concentration of active ingredient (ppm) | Prevention value (%) |
|---|---|---|
| 3 | 200 | 99 |
| 12 | 200 | 99 |
| 26 | 200 | 95 |
| 30 | 200 | 92 |
| 38 | 200 | 96 |
| 40 | 200 | 99 |
| 43 | 200 | 92 |
| 45 | 200 | 95 |
| 51 | 200 | 99 |
| 52 | 200 | 99 |
| 57 | 200 | 97 |
| 60 | 200 | 99 |
| 78 | 200 | 93 |
| A | 200 | 15 |
| B | 200 | 0 |

TABLE 9-continued

| Compound No. | Concentration of active ingredient (ppm) | Prevention value (%) |
|---|---|---|
| C | 200 | 0 |

What is claimed is:

1. A pyrazole derivative of formula (II):

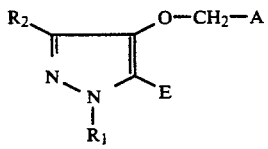

wherein:
$R_1$ and $R_2$ are independently hydrogen or $C_1$–$C_5$ alkyl;
A is a group of formula

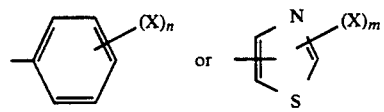

wherein x is independently hydrogen; halogen; cyano; nitro; $C_1$–$C_{10}$ alkyl, $C_2$–$C_{11}$ alkenyl, $C_1$–$C_{10}$ alkoxy, $C_2$–$C_{11}$ alkenyloxy, $C_2$–$C_{11}$ alkynyloxy, $C_2$–$C_{11}$ alkylcarbonyl or $C_2$–$C_{11}$ alkylcarbonyloxy optionally substituted with one or more substituents selected from halogen, nitro, cyano, trifluoromethyl and $C_1$–$C_5$ alkoxy; or $C_7$–$C_{13}$ arylcarbonyl, $C_4$–$C_9$ cycloalkylcarbonyloxy, $C_7$–$C_{13}$ arylcarbonyloxy, $C_6$–$C_{12}$ aryl, $C_6$–$C_{12}$ aryloxy, $C_2$–$C_{13}$ heteroaryl having 1-3 heteroatom(s) selected from oxygen, sulfur, and nitrogen, $C_2$–$C_{13}$ heteroaryloxy having 1-3 heteroatom(s) selected from oxygen, sulfur, and nitrogen, $C_7$–$C_{12}$ aralkyl or $C_7$–$C_{12}$ aralkyloxy optionally substituted with one or more substituents selected from halogen, nitro, cyano, trifluoromethyl, $C_1$–$C_5$ alkyl, and $C_1$–$C_5$ alkoxy; m is 1 or 2; and n is an integer of 1-5; or two Xs may form a fused ring together with the benzene ring or thiazole ring to which they are attached; and
E is ethoxycarbonyl or —$CH_2$—B wherein B is methoxycarbonyl or cyano.

2. A pyrazole derivative of formula (II) as claimed in claim 1, in which A is a group of formula:

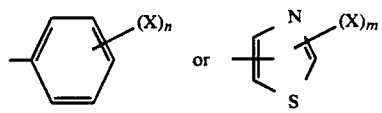

wherein X is independently hydrogen; halogen; cyano; nitro; $C_1$–$C_4$ alkyl, $C_2$–$C_3$ alkenyl, $C_1$–$C_3$ alkoxy, $C_2$–$C_3$ alkenyloxy, $C_2$–$C_3$ alkynyloxy, or $C_2$–$C_5$ alkylcarbonyloxy optionally substituted with one or more substituents selected from halogen, nitro, cyano, and trifluoromethyl; or phenyl, phenoxy, benzyl, benzyloxy, thiazolyl, thiazolyloxy, pyridyloxy, benzoyl, or benzothiazolyloxy optionally substituted with one or more substituents selected from halogen, nitro, cyano, trifluoromethyl, $C_1$–$C_4$ alkyl and $C_1$–$C_4$ alkoxy; m is 1 or 2; and n is an integer of 1-5; or two Xs may form a fused ring together with the benzene ring or thiazole ring to which they are attached, where the fused ring is selected from 2,3-dihydrobenzofuran, chroman, naphthalene, fluorene, anthraquinone or benzo-1,3-dioxole.

* * * * *